(12) United States Patent
Zhu et al.

(10) Patent No.: US 7,658,916 B2
(45) Date of Patent: Feb. 9, 2010

(54) METHODS OF ENHANCING LYSOSOMAL STORAGE DISEASE THERAPY BY MODULATION OF CELL SURFACE RECEPTOR DENSITY

(75) Inventors: Yunxiang Zhu, Wayland, MA (US); Seng H. Cheng, Wellesley, MA (US)

(73) Assignee: Genzyme Corporation, Cambridge, MA (US)

( * ) Notice: Subject to any disclaimer, the term of this patent is extended or adjusted under 35 U.S.C. 154(b) by 209 days.

(21) Appl. No.: 10/408,670

(22) Filed: Apr. 4, 2003

(65) Prior Publication Data

US 2004/0029779 A1    Feb. 12, 2004

Related U.S. Application Data

(60) Provisional application No. 60/370,747, filed on Apr. 5, 2002.

(51) Int. Cl.
- A61K 38/45    (2006.01)
- A61K 38/46    (2006.01)
- A61K 38/47    (2006.01)
- C12P 21/06    (2006.01)
- C12N 9/00    (2006.01)

(52) U.S. Cl. .................. 424/94.1; 424/94.6; 424/94.61; 435/69.1; 435/183; 435/195; 435/200

(58) Field of Classification Search ................ 424/94.1, 424/94.6, 94.61; 435/69.1, 183, 195, 200
See application file for complete search history.

(56) References Cited

U.S. PATENT DOCUMENTS

| 5,236,838 A | 8/1993 | Rasmussen et al. |
| 5,401,650 A | 3/1995 | Desnick et al. |
| 5,879,680 A | 3/1999 | Ginns et al. |

FOREIGN PATENT DOCUMENTS

| WO | WO 00/12740 | 3/2000 |
| WO | WO 00/34451 | 6/2000 |

OTHER PUBLICATIONS

East et al., The Mannose Receptor Family, Biochimica and biophysica acta 2002, 1572:364-386.*
Weiger PH, Galactosyl and N-AcetylGalactosaminyl Homeotastsis:A Funtion for Mammalian Asialoglycoprotein Receptor. BiEssays, 1994, 16:519-524.*
Rusittu el al., Modulation of cell surface expression of liver carbohydrate receptors during in vivo induction of apoptosis with lead nitrate. Cell Tissue Res, 1999, 298: 105-112.*
Devirgiliis L Conti , Bruscalupi G, Dini L, Modulation of asialoglycoprotein binding activity in livers of pregnant or estrogen-treated rats. Biosci Rep. 1989 9:701-7.*
Doyle AG, Herbein G, Montaner LJ, Minty AJ, Caput D, Ferrara P, Gordon S. Interleukin-13 alters the activation state of murine macrophages in vitro: comparison with interleukin-4 and interferon-gamma. Eur J lmmunol. 1994 ;24:1441-5.*
Stockert RJ, Morell AG.Second messenger modulation of the asialoglycoprotein receptor. J Biol Chem. 1990 265:1841-6.*
Weiss P, Ashwell G.The asialoglycoprotein receptor: properties and modulation by ligand. Prog Clin Biol Res. 1989;300:169-84.*
Weiss P, Ashwell G, Morell AG, Stockert RJ. Modulation of the asialoglycoprotein receptor in human hepatoma cells: effect of glucose. Hepatology. 1994 ;19:432-9.*
Eichbaum Q, Heney D, Raveh D, Chung M, Davidson M, Epstein J, Ezekowitz RA. Murine macrophage mannose receptor promoter is regulated by the transcription factors PU.1 and SP1. Blood. 1997 90:4135-43.*
Weigel PH, Yik JH. Glycans as endocytosis signals: the cases of the asialoglycoprotein and hyaluronan/chondroitin sulfate receptors. Biochim Biophys Acta. 2002 ;1572:341-63.*
Stryer, Biochemistry, third edition, W. H. Freeman and Company/New York, pp. 184-187.*
Bujanover et al., The effect of dexamethasone and glucagon on the expression of hepatocyte plasma membrane proteins during development. Hepatology. Jul.-Aug. 1988;8(4):722-7.PubMed 2899049, Abstract.*
Zhu et al., Dexamethasone-mediated up-regulation of the mannose receptor improves the delivery of recombinant glucocerebrosidase to Gaucher macrophages. J Pharmacol Exp Ther. Feb. 2004;308(2):705-11. Epub Nov. 10, 2003.*
Weinreb et al., Effectiveness of enzyme replacement therapy in 1028 patients with type 1 Gaucher disease after 2 to 5 years of treatment: a report from the Gaucher RegistryThe American Journal of Medicine, vol. 113, Issue 2, pp. 112-119.*

(Continued)

*Primary Examiner*—Maria Leavitt
(74) *Attorney, Agent, or Firm*—Hamilton, Brook, Smith & Reynolds, P.C.

(57) ABSTRACT

Methods of modulating uptake of extracellular lysosomal enzymes by administering a pharmaceutical agent and methods of treating a lysosomal storage disease (such as Gaucher disease, Pompe disease, Fabry disease or Niemann-Pick disease) or enhancing enzyme replacement therapy or gene therapy, comprising administering a pharmaceutical agent such as dexamethasone, glucose or insulin, are provided.

11 Claims, 10 Drawing Sheets

OTHER PUBLICATIONS

Charrow et al., The Gaucher Registry, demographics and disease, Archives of Internal Medicine 2000, pp. 2835-2843.*

Oqueh et al., Antenatal dexamethasone and the growth hormone-insulin-like growth factor axis.Hum Reprod. Jun. 2000 ;15(6):1403-6.*

Brieva et al., Effect of an inhaled glucocorticosteroid on airway mucosal blood flow in mild asthma.Am J Respir Crit Care Med. Jan. 2000;161(1):293-6.*

Nelson et al., Oral glucocorticosteroid-sparing effect of budesonide administered by Turbuhaler: a double-blind, placebo-controlled study in adults with moderate-to-severe chronic asthma. Pulmicort Turbuhaler Study Group.Chest. May 1998;113(5):1264-71.*

Richard et al., Antibody response in patients with Gaucher disease after repeated infusion with macrophage-targeted glucocerebrosidase.Blood. Sep. 1, 1993;82(5):1402-9.*

Greenspan, Appleton & Lange, 1991, pp. 323-340.*

Grabowski GA, et al., Enzyme therapy in type 1 Gaucher disease: comparative efficacy of mannose-terminated glucocerebrosidase from natural and recombinant sources.Ann Intern Med. Jan. 1, 1995;122(1):33-9.*

Barton NW, et al., Therapeutic response to intravenous infusions of glucocerebrosidase in a patient with Gaucher disease. Proc Natl Acad Sci U S A. Mar. 1990;87(5):1913-6.*

Anderson et al., Individualization of long-term enzyme replacement therapy for Gaucher diseaseGenetics in Medicine:vol. 7(2)Feb. 2005pp. 105-110.*

Watson et al. Recombinant DNA, second edition, 2001, pp. 453-455.*

Kornfeld, S. and Mellman, I., "The Biogenesis of Lysosomes," *Annual Review Cell Biology*, 5:483-525 (1989).

Friedman, B., et al., "A Comparison of the Pharmacological Properties of Carbohydrate Remodeled Recombinant and Placental-Derived β-Glucocerebrosidase: Implications for Clinical Efficacy in Treatment of Gaucher Disease," *Blood*, 93(9):2807-2816 (1999).

Clairmont, K.B., and Czech, M.P., "Insulin Injection Increases the Levels of Serum Receptors for Transferrin and Insulin-Like Growth Factor-II/Mannose-6-Phosphate in Intact Rats," *Endocrinology*, 127(4):1568-1573 (1990).

Zhou, M., et al., "Insulin-dependent Protein Trafficking in Skeletal Muscle Cells," *American Journal of Physiology (Endocrinology Metabol, 38)*, 275(2): E187-E196 (1998).

Villevalois-Cam, L., et al.,"Insulin-Induced Redistribution of the Insulin-Like Growth Factor II/Mannose 6-Phosphate Receptor in Intact Rat Liver," *Journal of Cellular Biochemistry*, 77:310-322 (2000).

Kandror, K.V. and Pilch, P.F., "The Insulin-like Growth Factor II/Mannose 6-Phosphate Receptor Utilizes the Same Membrane Compartments as GLUT4 for Insulin-dependent Trafficking to and from the Rat Adipocyte Cell Surface," *Journal of Biological Chemistry*, 271(36):21703-21708 (1996).

Zhang, Q., et al., "Glucose Increases Both the Plasma Membrane Number and Phosphorylation of Insulin-like Growth Factor II/Mannose 6-Phosphate Receptors," *Journal of Biological Chemistry*, 272(38):23703-23706 (1997).

He, X, et al., "Characterization of Human Acid Sphingomyelinase Purified from the Media of Overexpressing Chinese Hamster Ovary Cells," *Biochimica et Biophysica Acta*, 1432: 251-264 (1999).

Ceredase Prescribing Information, http://gaucher.mgh.harvard.edu/ceredaseprescribe,1995, Genzyme Corporation, retrieved on Jul. 8, 2003.

Cowan, H.B., et al., "Dexamethasone Up-Regulates Mannose Receptor Activity by Increasing mRNA Levels," *Archives of Biochemistry and Biophysics*, 296(1):314-320 (1992).

Stein, M., et al., "Interleukin 4 Potently Enhances Murine Macrophage Mannose Receptor Activity: A Marker of Alternative Immunologic Macrophage Activation," *Journal of Experimental Medicine*, 176:287-292 (1992).

Mokoena, T. and Gordon, S., "Human Macrophage Activation," *Journal of Clinical Investigation*, 75:624-631 (1985).

Schreiber, S., et al., "Regulation of Mouse Bone Marrow Macrophage Mannose Receptor Expression and Activation by Prostaglandin E and IFN-γ," *The Journal of Immunology*, 151(9):4973-4981 (1993).

Treichel, U., et al., "Effects of Cytokines on Synthesis and Function of the Hepatic Asialoglycoprotein Receptor," *Journal of Cellular Physiology*, 158:527-534 (1994).

Van Der Ploeg, A.T., et al., "Receptor-Mediated Uptake of Acid α-Glucosidase Corrects Lysosomal Glycogen Storage in Cultured Skeletal Muscle," *Pediatric Research*, 24(1): 90-94 (1988).

Van Der Ploeg, A.T., et al., "Intravenous Administration of Phosphorylated Acid α-Glucosidase Leads to Uptake of Enzyme in Heart and Skeletal Muscle of Mice," *Journal of Clinical Investigation*, 87: 513-518 (1991).

Zimran, A. et al., "Commentary: Low-Dose High-Frequency Enzyme Replacement Therapy Prevents Fractures Without Complete Suppression of Painful Bone Crises in Patients with Severe Juvenile Onset Type I Gaucher Disease," *BCMD*, 24(15): 303-305 (1998).

Cerezyme® (Imiglucerase for injection) product insert, Aug. 27. 1996.

Reuser, A., et al., "Enzyme Therapy for Pompe Disease: from Science to Industrial Enterprise," *European Journal of Pediatrics*, 161: S106-S111 (2002).

Van Hove, J.L.K.,et al., "High-Level Production of Recombinant Human Lysosomal Acid α-Glucosidase in Chinese Hamster Ovary Cells Which Targets to Heart Muscle and Corrects Glycogen Accumulation in Fibroblasts from Patients with Pompe Disease," *Proc. Natl. Acad. Sci.*, 93: 65-70 (1996).

Hirschhorn, R., "Glycogen Storage Disease Type II: Acid α-Glucosidase (Acid Maltase) Deficiency," *The Metabolic and Molecular Bases of Inherited Disease*, C. R. Scriver et al., eds. (NY: McGraw-Hill, Inc.), 2443-2464 (7$^{th}$ ed. 1995).

Ausems, M.G.E.M., et al., "Frequency of Glycogen Storage Disease Type II in the Netherlands: Implications for Diagnosis and Genetic Counselling," *European Journal of Human Genetics*, 7: 713-716 (1999).

Martiniuk, F. et al., "Carrier Frequency for Glycogen Storage Disease Type II in New York for Estimates of Affected Individuals Born with the Disease," *American Journal of Medical Genetics*, 79:69-72 (1998).

Fuller, M., et al., "Isolation and Characterisation of a Recombinant, Precursor Form of Lysosomal Acid α-Glucosidase," *Eur. J. Biochem.*, 234: 903-909 (1995).

Amalfitano, A., et al., "Recombinant Human Acid α-glucosidase Enzyme Therapy for Infantile Glycogen Storage Disease Type II: Results of a Phase I/II Clinical Trial," *Genetics in Medicine*, 3(2): 132-138 (2001).

Barton, N. W., et al., "Therapeutic Response to Intravenous Infusions of Glucocerebrosidase in a Patient with Gaucher Disease," *Proc. Natl. Acad. Sci. USA*, 87: 1913-1916 (1990).

Gewert, K., et al., "Dexamethasone Downregulates Lysosomal Secretion in Mouse Macrophages: Involvement of Signaling Through Protein Kinase C," *Journal of Inflammation*, 47: 115-125 (1995/1996).

Ezekowitz, R.A.B., and Gordon, S., "Interaction and Regulation of Macrophage Receptors," *Biochemistry of Macrophages*, 127-136 [Ciba Foundation Symposium 118] (Pitman, London) (1986).

"General Discussion 2", 137-140, accompanying Ezekowitz, R.A.B., and Gordon, S., "Interaction and Regulation of Macrophage Receptors," *Biochemistry of Macrophages*, 127-136 [Ciba Foundation Symposium 118] (Pitman, London) (1986).

Knolle, P.A., et al., "IL-10 Down-Regulates T Cell Activation by Antigen-Presenting Liver Sinusoidal Endothelial Cells Through Decreased Antigen Uptake Via the Mannose Receptor and Lowered Surface Expression of Accessory Molecules," *Clin. Exp. Immunol.*; 114: 427-433 (1998).

Harris, N., et al., "Characterization of the Murine Macrophage Mannose Receptor: Demonstration That the Downregulation of Receptor Expression Mediated by Interferon-γ Occurs at the Level of Transcription," *Blood*, 80(9): 2363-2373 (1992).

Schreiber, S., et al., "Prostaglandin E Specifically Upregulates the Expression of the Mannose-Receptor on Mouse Bone Marrow-Derived Macrophages," *Cell Regulation*, 1: 403-413 (1990).

Sato, Y. and Beutler, E., "Binding, Internalization, and Degradation of Mannose-terminated Glucocerebrosidase by Macrophages," *J. Clin. Invest.*, 91: 1909-1917 (1993).

Montaner, L. J., et al., "Type 1 and Type 2 Cytokine Regulation of Macrophage Endocytosis: Differential Activation by IL-4/IL-13 as Opposed to IFN-γ or IL-10," *J. Immun.*, 162: 4606-4613 (1999).

Braulke, T., et al., "Regulation of Mannose 6-Phosphate/Insulin-Like Growth Factor II Receptor Distribution by Activators and Inhibitors of Protein Kinase C," *Eur. J. Biochem.*, 189(3): 609-616 (1990).

Braulke, T., et al., "Insulin-Like Growth Factors I and II Stimulate Endocytosis but Do Not Affect Sorting of Lysosomal Enzymes in Human Fibroblasts," *J. Bio. Chem.*, 265(12): 6650-6655 (1990).

Hu, K., et al., "Modulation of the Insulin Growth Factor II/Mannose 6-Phosphate Receptor in Microvascular Endothelial Cells by Phorbol Ester via Protein Kinase C*," *J. Bio. Chem.*, 265(23): 13864-13870 (1990).

Lansink, M., et al., "Increased Clearance Explains Lower Plasma Levels of Tissue-Type Plasminogen Activator by Estradiol: Evidence for Potently Enhanced Mannose Receptor Expression in Mice," *Blood*, 94(4): 1330-1336 (1999).

Braulke, T., et al., "Regulation of the Mannose 6-Phosphate/IGF II Receptor Expression at the Cell Surface by Mannose 6-Phosphate, Insulin Like Growth Factors and Epidermal Growth Factor," The EMBO Journal, 8(3): 681-686 (1989).

McCarthy, T.L., et al., "Links Among Growth Factors, Hormones, and Nuclear Factors with Essential Roles in Bone Formation," *Crit. Rev. Oral Biol. Med.*, 11(4): 409-522 (2000).

Sex Steroid. Wikipedia [online]. [retrieved on Oct. 23, 2007]. Retrieved from the Internet <URL: http://en.wikipedia.org/wiki/Sex_steroid>.

Glucocorticoid. Wikipedia [online]. [retrieved on Oct. 23, 2007]. Retrieved from the Internet <URL: http://en.wikipedia.org/wiki/Glucocorticoids>.

* cited by examiner

METHODS OF ENHANCING LYSOSOMAL STORAGE DISEASE THERAPY BY MODULATION OF CELL SURFACE RECEPTOR DENSITY

RELATED APPLICATION

This application claims the benefit of U.S. Provisional Application No. 60/370,747 filed Apr. 5, 2002. The entire teachings of the above application are incorporated herein by reference.

BACKGROUND OF THE INVENTION

Lysosomal storage diseases are a group of rare genetic disorders comprising more than forty individual diseases. Currently, a promising treatment for these diseases is enzyme replacement therapy (ERT). Gene therapy, which employs a depot expression strategy where high-level expression of lysosomal enzymes in one organ can be secreted into the blood stream and carried to other organs for uptake, is another promising option. One of the major issues with ERT treatment for lysosomal storage diseases is that the infused lysosomal enzymes are rapidly removed from the blood stream by the liver, either through carbohydrate-binding receptors or non-specifically. For substrate deprivation and small molecule therapies, ERT, gene therapy, and combinations thereof, more efficient uptake of lysosomal enzymes circulating in the blood stream by target cells and/or organs would be desirable.

SUMMARY OF THE INVENTION

It has now been found that the uptake of extracellular lysosomal enzymes by cells can be increased by up-regulating the cell surface expression and density of carbohydrate binding receptors. For example, up-regulation of the mannose receptor on macrophage cells by a glucocorticosteroid such as dexamethasone, for example, increases the target organ uptake of glucocerebrosidase for the treatment of Gaucher disease (see, e.g., Examples 1 and 2). Furthermore, the dexamethasone-induced increase in glucocerebrosidase uptake is selective for macrophage cells, which are the cells most severely affected by Gaucher disease. Likewise, up-regulation of the mannose 6-phosphate/IGF-II receptor (M6P/IGF-II) by insulin/glucose on muscle cell surfaces increases target organ uptake of acid alpha-glucosidase which is needed for the treatment of Pompe's disease (see, e.g., Examples 3 and 4). Based on these discoveries, methods of treating lysosomal storage diseases are contemplated herein.

One embodiment of the invention is a method of modulating uptake of extracellular lysosomal enzymes in an animal in need of such modulation (i.e., an animal which is undergoing treatment, for example, for a lysosomal storage disease, comprising administering to the animal an effective amount of at least one pharmaceutical agent which selectively modulates the cell surface density of carbohydrate-binding receptors on the surface of target cells. The pharmaceutical agent is administered in an amount and for a duration effective to modulate receptor density for a clinically relevant and significant period of time prior to administration of the lysosomal enzyme.

The pharmaceutical agent can be any agent capable of modulating cell surface density of the carbohydrate receptors, including insulin, glucose, protein kinase C activator, insulin-like growth factors, glucocorticoid steroids, dexamethasone, prostaglandin E, cytokines, interleukin-4 and interleukin-13. Pharmaceutical agents also include small molecule anti-diabetic drugs (e.g., sulfonylurea or biguanides), including drugs which increase glucose transport on the surface of muscle cells. The pharmaceutical agent can selectively up-regulate the cell surface density of receptors for the lysosomal enzyme on the surface of target cells. The pharmaceutical agent can be administered via a variety of routes of administration, including but not limited to, orally, intramuscularly, intradermally, intravenously or interperitoneally.

Yet another embodiment of the invention is a method of treating a lysosomal storage disease in a patient (animal or human) comprising administering to the patient an effective amount of a lysosomal enzyme or functional equivalent thereof alleviate symptoms of the disease and an effective amount of a pharmaceutical agent which selectively modulates the cell surface density of receptors for the lysosomal enzyme on target cells.

In another embodiment of the present invention, the M6P/IGF-II receptors, e.g., on the surface of muscle cells, can be selectively up-regulated by a pharmaceutical agent, e.g., insulin, glucose, protein kinase C activator or insulin-like growth factor. For example, the pharmaceutical agent can be insulin and/or glucose. The lysosomal storage disease can be Pompe disease and the lysosomal enzyme can be acid alpha-glucosidase. The invention also relates to a method of treating Pompe disease in a patient comprising administering to the patient an effective amount of acid alpha-glucosidase and at least one pharmaceutical agent which up-regulates M6P/IGF-II receptors on the cell surface. The acid alpha-glucosidase can be administered to the patient by enzyme replacement therapy or gene therapy. The M6P/IGF-II receptors on the surface of muscle cells in the patient can be selectively up-regulated by the pharmaceutical agent. The target cells can also include affected skeletal and cardiac muscle cells. The pharmaceutical agent can be insulin or glucose or both. The invention also relates to a method of treating Fabry disease comprising administering to the patient an effective amount of alpha-galactosidase and a pharmaceutical agent which up-regulates M6P/IGF-II receptors for its uptake. In one embodiment, the agent is insulin, or glucose or both. The target cells can include affected cells in the kidney and heart.

Another embodiment of the invention is a method of increasing uptake of acid alpha-glucosidase or alpha galactosidase in a patient in need of such treatment, i.e., a patient who has a lysosomal storage disease, comprising administering an effective amount of insulin to the patient, wherein the insulin increases surface density of M6P/IGF-II receptors. Glucose can also be administered to the patient, e.g., prior to, or concurrently with, administration of the insulin to the patient.

In another embodiment, the mannose receptors, such as those on macrophage cell surfaces, can be selectively increased by a pharmaceutical agent, such as a glucocorticosteroid, dexamethasone, prostaglandin E, interleukin-4 or interleukin-13. In one embodiment, the pharmaceutical agent is dexamethasone. The lysosomal storage disease can also be Gaucher disease and the exogenous lysosomal enzyme can be CEREZYME® enzyme, a modified form of glucocerebrosidase or a functional equivalent thereof. CEREZYME® (imiglucerase for injection) is a trademarked product of Genzyme Corporation, and is a modified form of the enzyme glucocerebrosidase. The invention herein is applicable to all glucocerebrosidase in all forms. CEREZYME® is one example of glucocerebrosidase. The invention also relates to a method of treating Gaucher disease in a patient comprising administering to the patient an effective amount of a pharmaceutical agent which increases the surface density of mannose receptors in the patient, and CEREZYME® enzyme, modified glucocerebrosidase or a functional equivalent thereof. The pharmaceutical agent can be administered prior to the CEREZYME® enzyme, modified glucocerebrosidase or functional equivalent thereof. A functional equivalent is one that possesses a similar enzymatic activity as glucocerebrosidase and that exhibits sufficient specificity for the substrate, which is glucocerebroside.

In yet another embodiment, cell surface density of receptors on non-target cells is decreased. For example, mannose receptors and asialoglycoprotein receptors can be decreased when the subject has a lysosomal storage disease that can be treated by a lysosomal enzyme specific for an M6P receptor such as M6P/IGF-II receptor. The decreasing agent can optionally be co-administered with the lysosomal enzyme and/or with an agent that up-regulates the M6P/IGF-II receptor on target cells. Thus, the decrease of cell surface density of mannose receptors on non-target cells can be accompanied by an increase of cell surface density of M6P/IGF-II receptors on target cells, e.g., muscle cells.

Yet another embodiment of the invention encompasses methods of increasing efficacy of a lysosomal enzyme replacement therapy comprising administering to a patient undergoing such therapy an effective amount of a pharmaceutical agent which increases cell surface receptors for lysosomal enzymes administered during or prior to the enzyme replacement therapy. The pharmaceutical agent can selectively increase cell surface receptors for lysosomal enzymes on target cells. The target cells can be muscle cells or macrophages.

BRIEF DESCRIPTION OF THE DRAWINGS

FIG. 1A is representative of several experiments that gave similar results. Error bars are expressed as standard deviation. Mannan represents yeast mannan, a mannose receptor inhibitor.

FIG. 1B is representative of several experiments that gave similar results. Error bars are expressed as standard deviation.

DETAILED DESCRIPTION OF THE INVENTION

Described herein are methods to enhance the efficiency of enzyme replacement therapy (ERT) and gene therapy to treat lysosomal storage diseases by manipulating cell surface receptors to increase the uptake of lysosomal enzymes into affected (target) cells of patients.

The invention described herein encompasses methods of treating lysosomal storage diseases, including Gaucher disease, Fabry disease and Pompe disease, for example, by regulating lysosomal enzyme receptors to increase uptake of beneficial enzymes into desired cells. For treatment of Gaucher disease, increasing uptake of lysosomal enzymes through the mannose receptor is desirable. For treatment of Pompe disease and Fabry disease, increasing uptake of lysosomal enzymes through the M6P/IGF-II receptor (CI-MPR), and also decreasing the densities of mannose receptors (MRs) and asialoglycoprotein receptors (ASGPRs) in liver cells and/or by increasing the density of the M6P/IGF-II receptors on the cell surface of desired cells would be very beneficial.

Gaucher disease is caused by a deficiency of glucocerebrosidase that catalyzes biodegradation of a lipid, glucocerebroside (GL1). This deficiency causes harmful quantities of glucocerebroside to accumulate in the spleen, liver, lungs, bone marrow, and, in rare cases, the brain. Enzyme replacement therapy is particularly effective for Gaucher disease patients who do not have nervous system complications. For example, CEREZYME® enzyme (imiglucerase), a recombinant, modified form of the enzyme glucocerebrosidase, can be administered. The major target tissues for Gaucher disease ERT are the liver, spleen and bone marrow, wherein the macrophage cells are severely affected by the accumulation of glucocerebroside.

As described herein in Example 1, dexamethasone was found to have differential effects on CEREZYME® enzyme uptake by the representative liver cells. The dexamethasone treatment of macrophage cells enhanced CEREZYME® enzyme uptake by about 3-5-fold compared to non-treated cells. In a separate experiment, dexamethasone increased the uptake of CEREZYME® enzyme by rat alveolar macrophage cells (ATCC# NR8383) by about 250-350% after two days. However, dexamethasone did not significantly enhance the mannose receptor-mediated uptake of CEREZYME® enzyme by liver endothelial cells or by hepatocytes, indicating that dexamethasone selectively increased CEREZYME® enzyme uptake in the desired macrophage cells. (See FIGS. 1A-1F).

Figure 2:
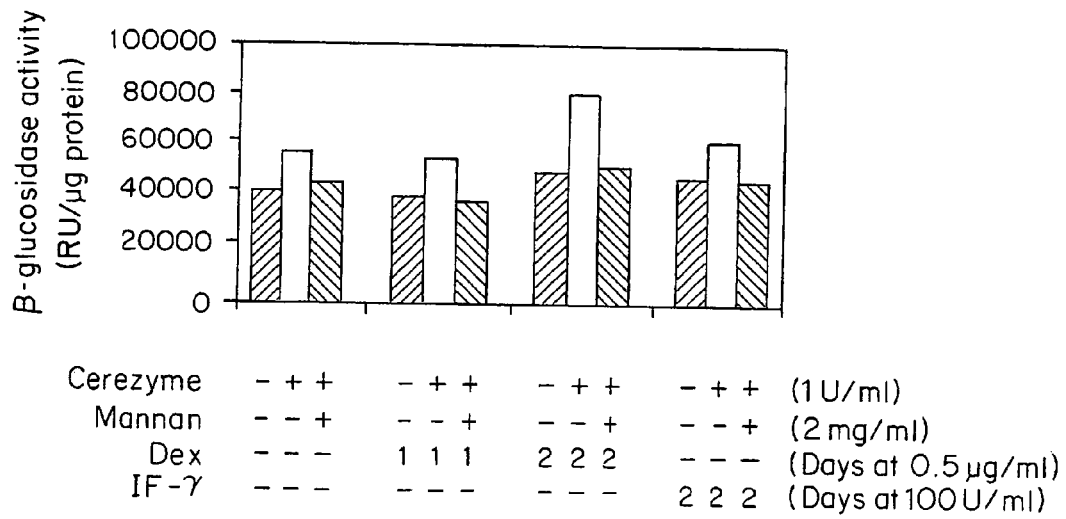
FIG. 2 depicts the effects of time of dexamethasone treatment and interferongamma (IF-γ) on CEREZYME® enzyme uptake by macrophages.

The species specificity of dexamethasone's effects was also tested. Interferon-gamma is known to downregulate mannose receptor expression on macrophage cells in a species-specific manner (Mokoena, et al., *J Clin Investigation* 75:624-631 (1985)). For example, mouse interferon-gamma will not act on macrophages from other species such as rats. As expected, mouse interferon-gamma did not enhance or inhibit CEREZYME® enzyme uptake by rat macrophage cells (FIG. 2, last bar group). In contrast, dexamethasone enhanced the CEREZYME® enzyme uptake by the rat macrophage cells, suggesting that dexamethasone's effect is not species-specific.

The effects of prostaglandin E on macrophage cell uptake of CEREZYME® enzyme were also evaluated using the same experimental protocol as that indicated in Example 1, with the exception that prostaglandin E was substituted for dexamethasone. Prostaglandin E has also been shown to increase mannose receptor expression (Schreiber, S., et al., *The Journal of Immunology*, 151(9):4973-4981 (1993)). A similar stimulative effect as with dexamethasone was observed.

Figure 3:
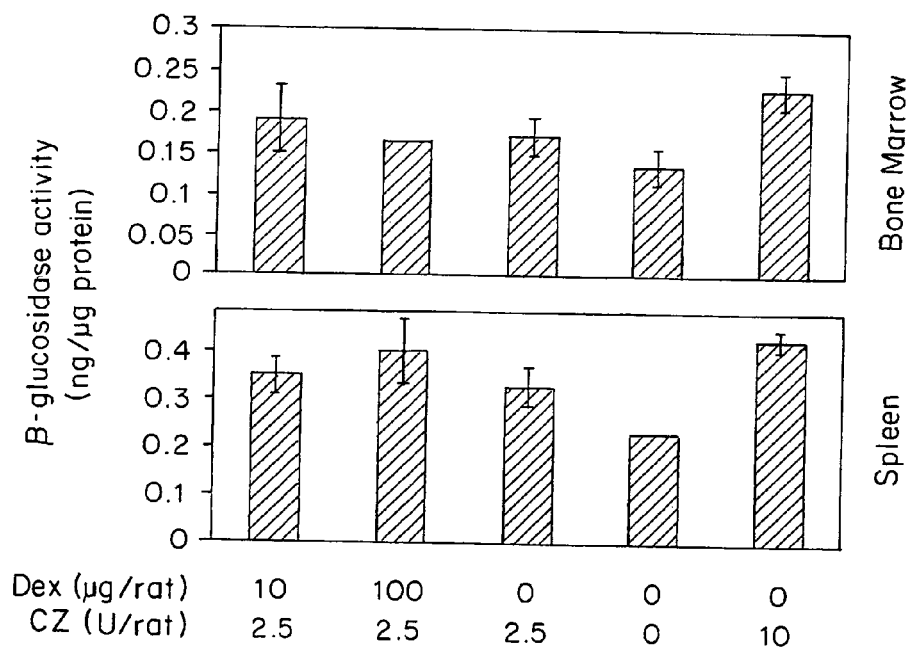
FIG. 3 depicts the effects of dexamethasone on CEREZYME® enzyme uptake in rat tissues. Upper panel: bone marrow. Lower panel: spleen.
Figure 4A:
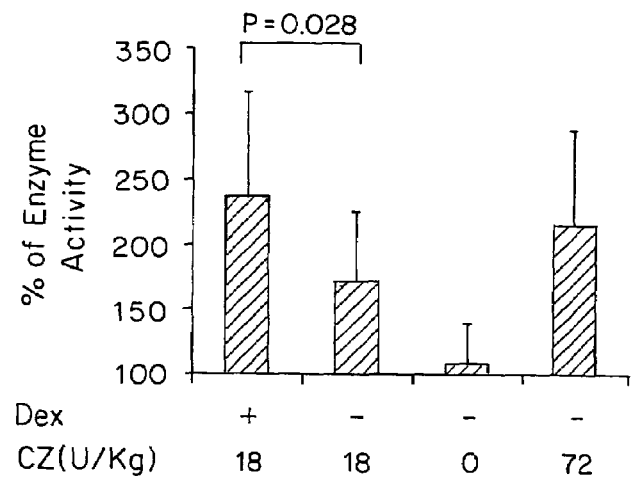
FIG. 4A depicts the increase of CEREZYME® enzyme uptake by isolated spleen macrophages from rats pretreated with dexamethasone. The figure is a summary of two similar experiments, with a total of 10 rats in each group. Two data points in the dexamethasone pretreated group, one in the non-treated control group and one in the positive control group were deleted due to GC activities that were less than the endogenous control, p<0.05.
Figure 4B:
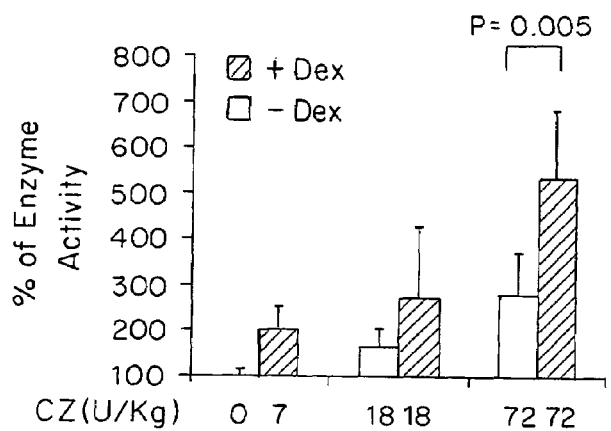
FIG. 4B depicts the increase of CEREZYME® enzyme uptake by isolated spleen macrophages from rats pretreated with dexamethasone at different CEREZYME® cn=6, p<0.005.
Figure 5:
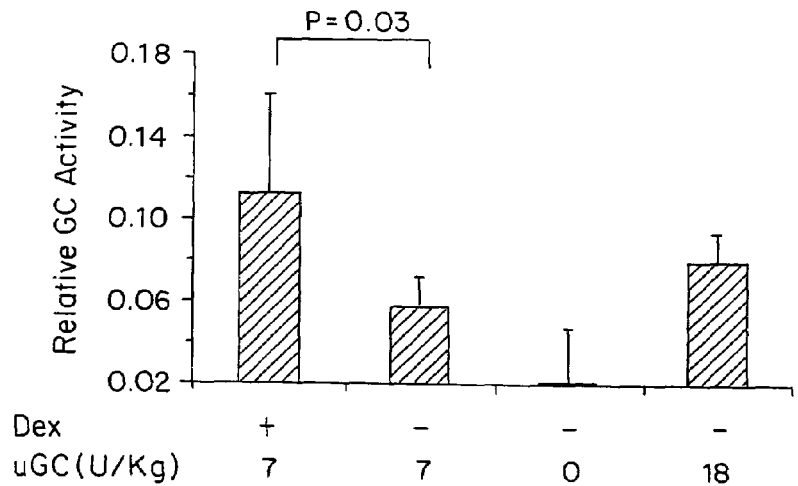
FIG. 5 depicts the increase of unmodified glucocerebrosidase enzyme uptake by spleen macrophages in rats pretreated with dexamethasone. The figure represents one of two experiments with a total of 10 rats in each group. p=0.03.
Figure 6:
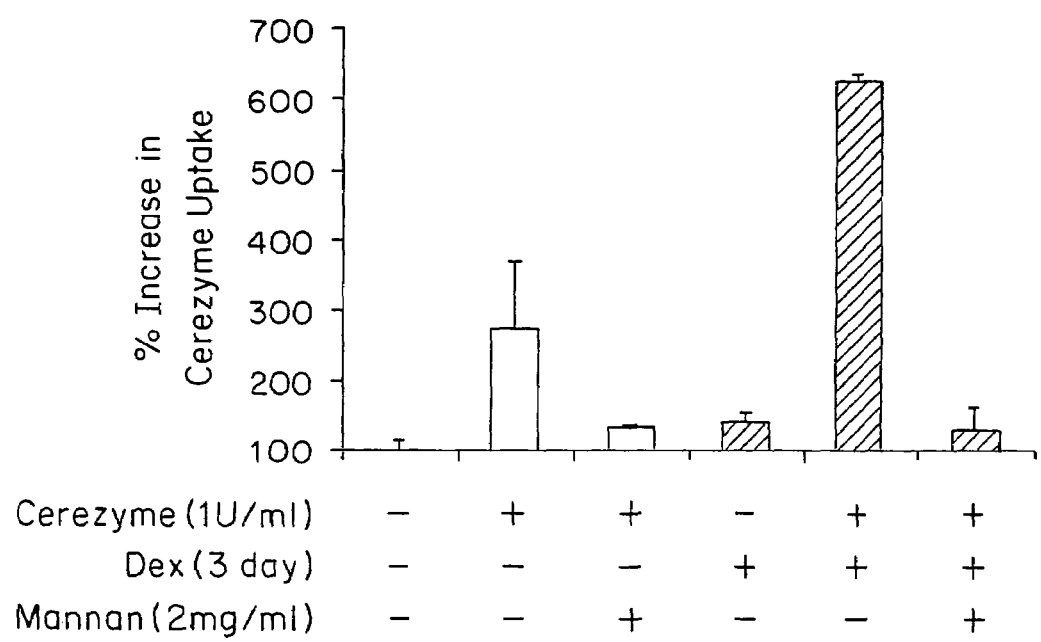
FIG. 6 depicts the increase of CEREZYME® enzyme uptake into lipid-filled lung alveolar macrophages isolated from acid sphingomyelinase knockout mice pretreated with dexamethasone. N=3, error bars are expressed as standard deviation.

As described herein in Example 2, after dexamethasone's effects in vitro were confirmed, its effects on CEREZYME® enzyme uptake in vivo were examined. There was a clear trend that dexamethasone treatment enhanced CEREZYME® enzyme uptake by Kupffer cells in the rat liver in vivo. In addition, the enhanced uptake of CEREZYME® enzyme by the dexamethasone-treated macrophages contributed to the increased total glucocerebrosidase activity in the spleen (FIGS. 3, 4A and 4B). Furthermore, dexamethasone pretreatment in rats also led to an increase in uptake of unmodified glucocerebrosidase enzyme by spleen macrophages (FIG. 5). The receptor up-regulation also occurred in diseased mouse lung alveolar macrophage cells. The cells of the mice pretreated with dexamethasone had a much stronger uptake of CEREZYME® enzyme than the cells of the control mice (FIG. 6).

In addition to Gaucher disease, the methods described herein can be used for the treatment of Pompe disease and Fabry disease. Pompe disease (also known as Glycogen storage disease type II (GSD-II) or acid maltase deficiency) is caused by a deficiency of acid α-glucosidase (GAA), a glycogen degrading lysosomal enzyme (Hirschhorn, R., "Glycogen storage disease type II: acid α-glucosidase (acid maltase) deficiency", in Scriver, C. R. et al, (eds) *The Metabolic and Molecular Basis of Inherited Disease*, 7$^{th}$ Ed., McGraw-Hill, New York, 1995, pp. 2443-2464). The deficiency results in excess glycogen accumulation in the lysosomes of almost all body tissues, with cardiac and skeletal muscle being the most seriously affected. Glycogen also accumulates in the liver and nerves. (Martiniuk, F. et al., *Amer. J. Med. Genet.* 79:69-72 (1998); Ausems, M. G. E. M. et al., *Eur. J. Hum. Genet.* 7:713-716 (1999)).

With Pompe disease, a desired outcome is improved delivery of GAA to the cardiac and skeletal muscle cells. To illustrate the potential of up-regulating the M6P/IGF-II receptor, examples are shown demonstrating improved uptake of another lysosomal enzyme, alpha-galactosidase.

Figure 7A:
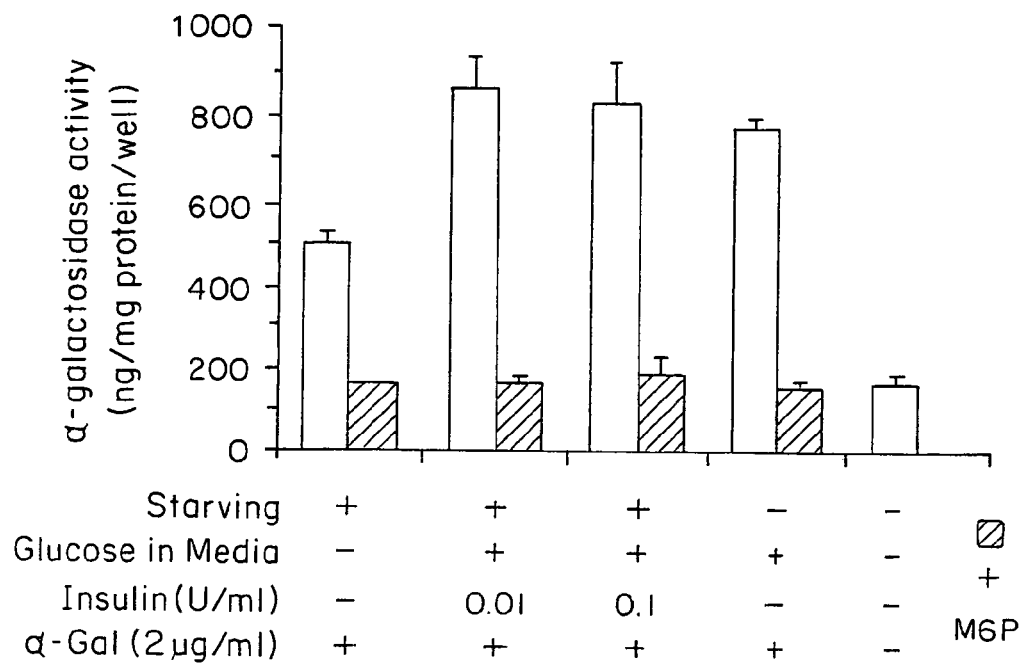
FIGS. 7A and B depict the increase of alpha-galactosidase (α-Gal) uptake into L6 myotubes after insulin/glucose stimulation in vitro.
Figure 7B:
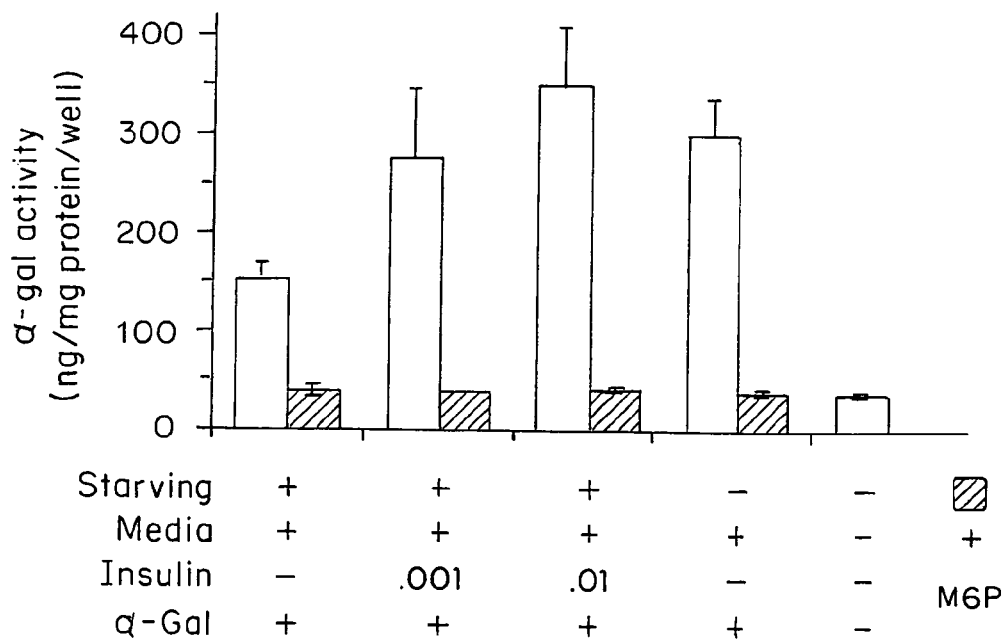
Figure 8:
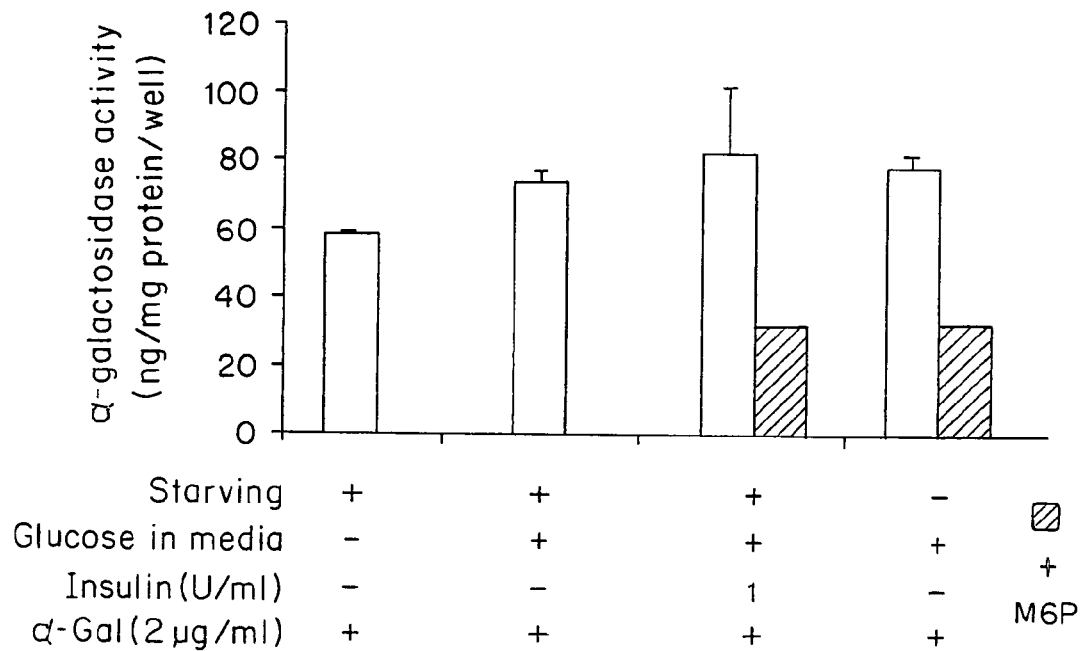
FIG. 8 depicts the effects of insulin on alpha-galactosidase uptake by Hep 3B cells in vitro.

As described herein in Example 3, insulin treatment stimulated M6P/IGF-II receptor-mediated uptake of alpha-galactosidase by muscle cells and hepatocytes in vitro (See FIGS. 7A, 7B and 8). In a separate experiment, insulin treatment increased alpha-galactosidase uptake by normal fibroblast, Fabry fibroblast and Hep 3B cells to about 200% (See FIG. 9).

Figure 10:
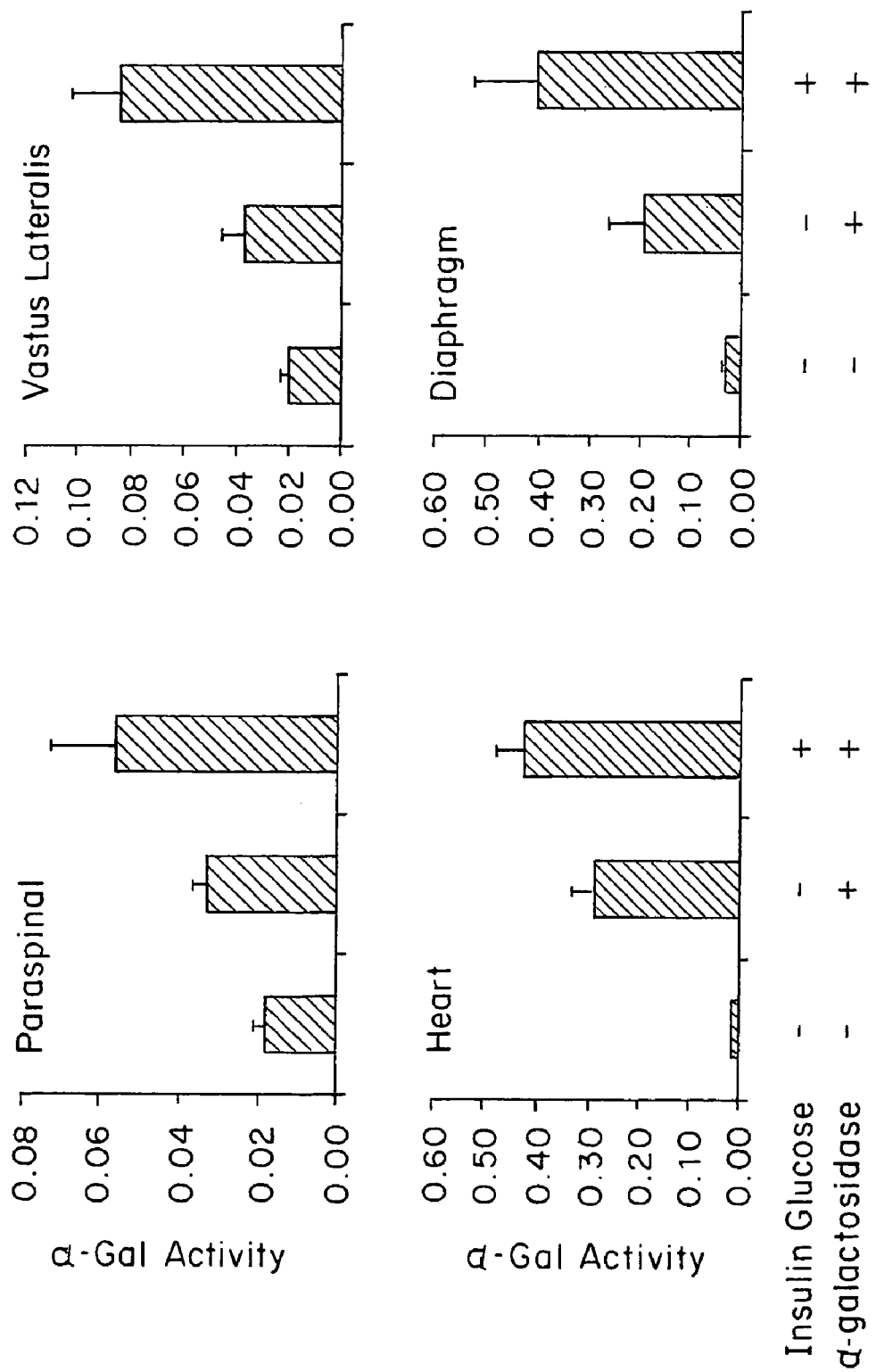
FIG. 10 depicts the increase of alpha-galactosidase uptake into different muscle tissues in normal mice after insulin/glucose stimulation in vivo.
Figure 11:
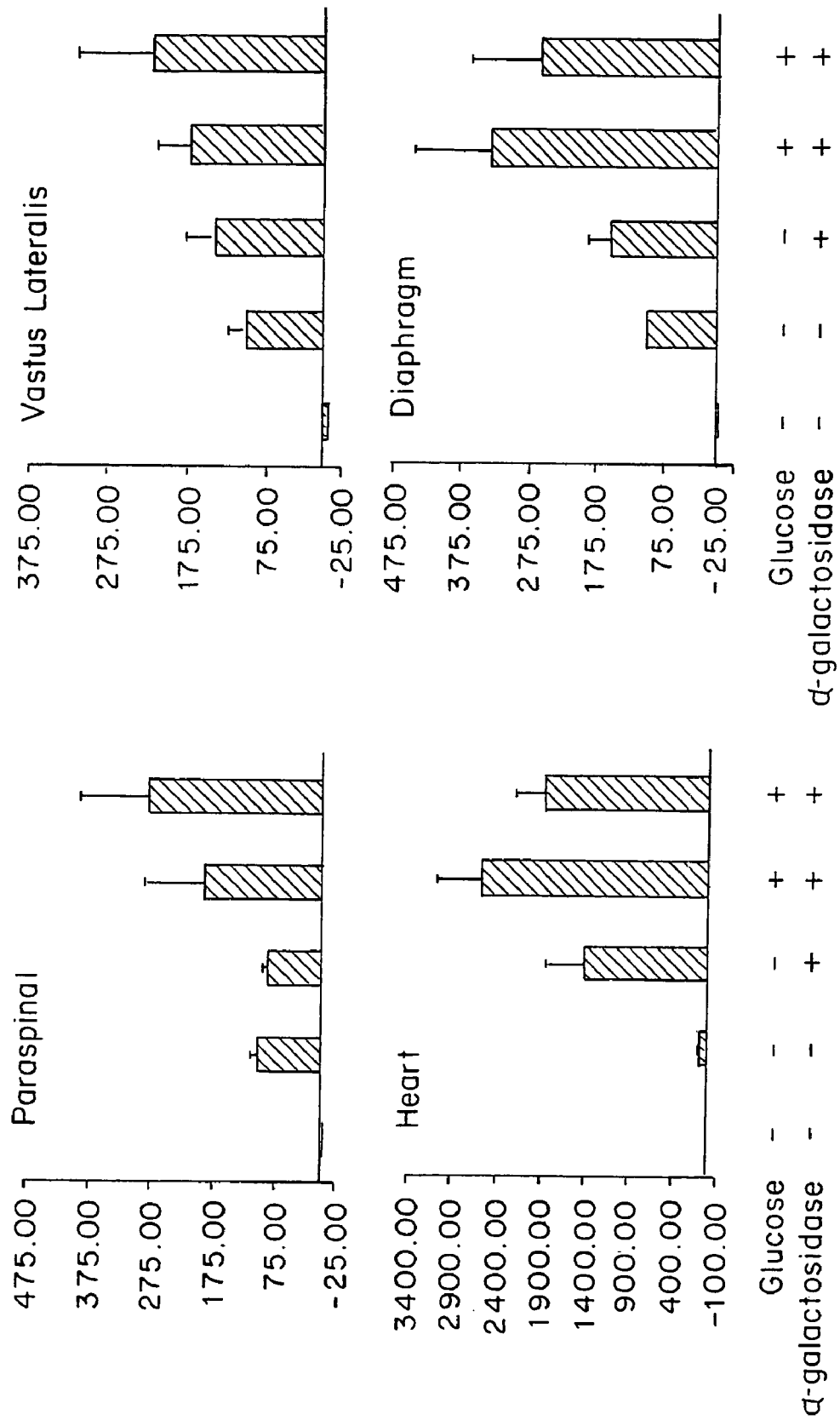
FIG. 11 depicts the increase of alpha-galactosidase uptake into different muscle tissues in Fabry mice after insulin/glucose stimulation in vivo.

As described herein in Example 4, insulin/glucose also increased the muscle up-take of alpha-galactosidase in vivo in normal mice (see FIG. 10) and Fabry mice (see FIG. 11).

Included in the present invention are methods of treating a lysosomal storage disease in an animal, by administering to the animal an effective amount of a (at least one) pharmaceutical agent and a (at least one) lysosomal enzyme or equivalent thereof. Other lysosomal storage diseases include Fabry disease, Schindler disease, Niemann-Pick disease, Morquio disease, Batten disease, Maroteaux-Lamy disease, metachromatic leukodystrophy disease, Hunter Syndrome and Hurler's disease.

The terms "treat" and "treatment," as used herein, refer to the alleviation, e.g., amelioration of one or more symptoms or effects associated with the disease, prevention, inhibition or delay of the onset of one or more symptoms or effects of the disease, and/or lessening of the severity or frequency of one or more symptoms or effects of the disease, such as the symptoms and effects described herein.

Gaucher disease treatment can result in reduction in liver size, spleen size or skeletal abnormalities and reversal, prevention, delay or lessening of abnormal blood counts and other manifestations of the disorder. For example, individuals with Type 1 Gaucher disease may experience enlargement of the liver and spleen leading to abdominal problems, weakening of the skeleton, and lung and kidney impairment. The presence of excessive amount of glucocerebroside in the bone marrow can interfere with production of red blood cells, resulting in anemia. It can also interfere with production of white blood cells and platelets, resulting in bruising, pallor, weakness, fatigue, susceptibility to infection, poor blood clotting, long clotting times and excessive bleeding. The glucocerebroside can also trigger the loss of minerals in the bones, causing the bones to weaken, and can interfere with the bone's blood supply, causing areas of bone death, or "infarctions", often leading to damage to the shoulder or hip joints, and a demineralization of the bones (osteoporosis). The weakening of the bones can lead to spontaneous fractures. Bone abnormalities may also cause pain ("bone crises") and swelling in the joints. Individuals with Gaucher disease may also have an increased cancer risk.

In addition to these symptoms, Type 2 and Type 3 Gaucher disease result in severe neurological impairment and/or early death. Type 2 (the infantile or acute neuropathic form), is characterized by brainstem and nervous system impairment, and can be fatal during the first three years of life. The neurologic symptoms of Type 3 (the juvenile or chronic neuropathic form) appear later in childhood, and include incoordination, mental deterioration, and myoclonic seizures. There is a subclassification of Type 3, called Norbottnian Gaucher disease, in which the slowly progressive neurological symptoms may not occur until early adulthood.

Pompe disease treatment can result in improvement of cardiac status or of pulmonary function, improvement in neurodevelopment and/or motor skills, reduction of glycogen levels in tissue of the individual affected by the disease or any combination of these effects, or a prevention, delay, lessening or reversal of other manifestations of the disorder. For example, in the infantile form (in which typically less than 1% of normal acid alpha-glucosidase activity is present), Pompe disease patients are affected by a hypertrophic cardiomyopathy, generalized muscle weakness and hypotonia secondary to massive glycogen accumulation in cardiac and skeletal muscles. The disease progresses rapidly, with death from cardiac failure usually occurring by one year of age. Juvenile (1-10% of normal acid alpha-glucosidase activity) and adult-onset (10-40% of normal acid alpha-glucosidase activity) forms of the disease are characterized by lack of severe cardiac involvement, later age of onset, and slower progression, but eventual respiratory or limb muscle involvement results in significant morbidity and mortality.

Treatment of Fabry disease (a disorder caused by a deficiency of alpha-galactosidase A, an enzyme involved in the biodegradation of lipids, leading to an accumulation of glycolipid) can result in reversal, prevention, delay, or lessening of any of the symptoms and manifestations of Fabry disease. For example, in Fabry disease, the accumulation of glycolipid can cause angiokeratomas, noncancerous skin growths, to form over the lower part of the trunk. A burning sensation may develop in the hands, feet, arms and legs, and the patient may have episodes of fever. Patients may also have gastrointestinal difficulties. The patient's corneas can become cloudy, resulting in poor vision. Patients may have impaired arterial circulation leading to early heart attacks and strokes. The kidneys may become progressively involved. Kidney failure, heart disease, or stroke, any of which may result from high blood pressure, can cause death.

The terms "improve", "increase" or "reduce," as used herein, indicate values that are relative to a baseline measurement, such as a measurement in the same individual prior to initiation of the treatment described herein, or a measurement in a control individual (or multiple control individuals) in the absence of the treatment described herein. A control individual is an individual afflicted with the same form of lysosomal storage disease as the individual being treated, who is about the same age as the individual being treated (to ensure that the stages of the disease in the treated individual and the control individual are comparable).

Also encompassed in the invention are methods of increasing efficacy of a therapy, e.g., substrate deprivations and small molecule therapies, lysosomal enzyme replacement therapy (ERT) or gene therapy, or any other form of therapy where the levels of enzyme naturally occurring in a patient are supplemented, comprising administering to a patient undergoing such therapy an effective amount of a pharmaceutical agent which increases cell surface receptors for lysosomal enzymes administered during or prior to the therapy.

Also encompassed herein are methods to reduce the amount or degree of lysosomal enzyme administration needed to treat individuals with lysosomal storage diseases. For example, included herein are: methods to increase the length of time between one administration of the lysosomal enzyme and the next (e.g., from two weeks to either three or four weeks); methods to reduce the dose of lysosomal enzyme necessary during each administration (e.g. from between 10-20 U/kg to below 10 U/kg); and methods to shorten the length of time spent during each administration (e.g., infusion) of the lysosomal enzyme (e.g., from two hours to less than one hour). Any of these desirable effects can occur separately or in any combination.

Substrate deprivation therapy includes administration of substrate deprivation compounds, including inhibitors of the enzyme UDP-glucose: N-acylsphingosine glucosyltransferase (GlcCer synthase). Compounds which inhibit GlcCer synthase can lower glycosphingolipid (GSL) concentrations. A number of potent inhibitors of GlcCer, referred to herein as "amino ceramide-like compounds," are disclosed, for example, in U.S. Pat. Nos. 6,051,598; 5,952,370; 5,945,442; 5,916,911 and 6,030,995, the teachings of which are incorporated by reference herein in their entirety.

Gene therapy can give the patient the ability to produce the lysosomal enzyme not produced by the defective gene. Gene therapy requires successful transfection of target cells in a patient. Transfection may generally be defined as the process of introducing an expressible polynucleotide (for example a gene, a cDNA, or an mRNA patterned thereon) into a cell. Successful expression of the encoding polynucleotide leads to production in the cells of a normal protein and leads to correction of the disease state associated with the abnormal gene.

The animal being treated can be a patient, i.e., an individual (e.g., fetus, child, adolescent, or adult human) having a lysosomal storage disease, e.g., Gaucher disease (i.e., Type 1, 2 or 3) or Pompe disease (i.e., either infantile, juvenile, or adult-onset). Typically the patient is an individual with normal glucose tolerance, e.g., a non-diabetic. The patient can be an individual who tolerates administration of the lysosomal enzyme without developing an adverse immune response. The individual can have low or residual lysosomal enzyme activity, or no measurable activity. In one embodiment, the animal is an individual who has been recently diagnosed with the disease. The present invention has application for both human and veterinary use. As defined herein, a patient "in need of" a treatment or method herein is a patient who has a lysosomal storage disease.

The pharmaceutical agent is a pharmaceutically acceptable compound which selectively modulates (i.e., affects or regulates) the cell surface density of receptors for the lysosomal enzyme, e.g., carbohydrate-binding receptors, on the surface of target cells. Pharmaceutical agents have been shown to affect cell surface carbohydrate-binding receptor expression. For example, a number of agents have been shown to up-regulate the M6P/IGF-II receptor, including insulin (Clairmont K B, Czech M P, *Endocrinology*, 127(4), 1568-1573 (1990); Zhou, M., et al., *American Journal of Physiology* (Endocrinology Metabolism, 38), E187-E196 (1998); Villevalois-Cam L. et al. *Journal of Cellular Biochemistry*, 77, 310-322 (2000); and Kandror, K. V. and Pilch P F., *Journal of Biological Chemistry*, 271(36), 21703-21708 (1996)); glucose (Zhang Q. et al. *Journal of Biological Chemistry*, 272(38), 23703-21706 (1997)); protein kinase C activator (Brulke, T. et al., *European Journal of Biochemistry* (1990) and Hu K. et al. *Journal of Biological Chemistry*, 265(23), 13864-13870 (1990)); and insulin-like growth factors (Brulke, T. et al. *Journal of Biological Chemistry*, 265(12), 6650-6655 (1990); and Brulke, T. et al. *EMBO Journal*, 8, 681-686 (1989)).

A number of other agents have been shown to up-regulate mannose receptor cell surface expression, including dexamethasone (Cowan, H. B., et al. *Archives of Biochemistry and*

Biophysics, 296, 314-320) (1992); Stein, M. et al. *Journal of Experimental Medicine*, 176, 287-292 (1992)); prostaglandin E (Schreiber, S. et al., *The Journal of Immunology*, 151(9), 4973-4981 (1993)); and interleukin-4 or 13 (Montaner, L. J., et al. *The Journal of Immunology*, 162, 4606-4613 (1999); Stein M. et al. *Journal of Experimental Medicine*, 176, 287-292 (1992)). Pharmaceutical agents also include small molecule anti-diabetic drugs (e.g. sulfonylureas or biguanides), including drugs which increase glucose transport on the surface of muscle cells.

In Gaucher disease, where glucocerebrosidase does not contain phosphate, targeting of this enzyme to macrophages can be achieved through mannose receptor-mediated endocytosis by remodeling of the carbohydrate to terminal mannose. Prostaglandin E series have been shown to enhance mannose receptor cell surface expression on macrophages by about 4-6-fold, interleukin-4 by 10-15-fold and dexamethasone by 3-fold.

Interferon-α and γ (interferon-alpha and interferon-gamma) have been shown to down-regulating mannose receptor (Mokoena, T., Gordon, S. *Journal of Clinical Investigation*, 75 624-631 (1985); Schreiber, S. et al. *The Journal of Immunology*, 151(9), 4973-4981 (1993)). Interferon alpha and gamma or interleukin-2 can down-regulate asialoglycoprotein receptors (ASGPR) and inhibit binding and uptake of asialoglycoproteins by 50% after 3-6 hour treatment and nearly 100% after 24 hour treatment (Treichel, U. et al., *Journal of Cellular Physiology*, 158, 527-534 (1994)). These agents can be used to treat Pompe and Fabry diseases by down-regulating mannose receptors (MR) and asialoglycoprotein receptors (ASGPR) and reducing clearance.

The down-regulation of asialoglycoprotein receptors in vivo may be beneficial to the efficient uptake of enzymes by target tissues through M6P/MPR by reducing competition for enzyme uptake. The effects of interferon alpha and gamma and interleukin-2 can be evaluated in vitro for effects on ASGPR on hepatocyte-derived cell lines and also for effects on M6P/IGF-II receptor on a number of different cells. In addition, the down-regulation of mannose receptors may benefit the M6P/MPR-mediated targeting pathway by reducing competition for enzyme uptake. Since interferon-gamma down-regulates both asialoglycoprotein receptors and mannose receptors, its effects on different mannose receptor-positive macrophage/endothelial cell lines can be evaluated in vitro. Optionally, these agents can be combined with insulin and/or glucose, which increases uptake of alpha-galactosidase and alpha glucosidase by the relevant target cells.

Thus, the pharmaceutical agent can be, for example, insulin, glucose, protein kinase C activator, insulin-like growth factors, glucocorticoid steroids, dexamethasone, prostaglandin E, cytokines, interleukin-4 and interleukin-13.

The pharmaceutical agent modulates the cell surface density of carbohydrate-binding receptors or receptors for the lysosomal enzyme, on the surface of target cells. As used herein, "modulation" refers to alteration, e.g., up-regulation, down-regulation, increase or decrease. "Selective" refers to differential effect on specific cells, tissues, organs, etc. (e.g., target cells), as opposed to other cells, tissues or organs. For example, "selective modulation" of target cells can refer to modulation of these cells to a greater extent than modulation of cells which are not target cells. In some instances, it can refer to modulation of only target cells. Target cells, tissues or organs refer to those cells, tissues or organs upon which the effects of an agent are desirable. For example, target cells include those cells to which modulation of cell surface density of carbohydrate-binding receptors is desirable. For instance, the pharmaceutical agent increases cell surface density for carbohydrate binding receptors, preferably those carbohydrate binding receptors which bind the lysosomal enzyme. As described herein, receptors include, but are not limited to, mannose receptors (MR), asialoglycoprotein receptors (ASGPR) and M6P/IGF-II receptors (M6P/IGF-II receptors).

As used herein, the term "pharmaceutically acceptable", as it refers to compositions, carriers, diluents and reagents, means that the materials are capable of administration to or upon a mammal with a minimum of undesirable physiological effects such as nausea, dizziness or gastric upset.

The lysosomal enzyme can be in a form that, when administered, targets tissues such as the tissues affected by the disease (e.g., heart, muscle). The lysosomal enzyme can be administered alone or in a composition. The lysosomal enzyme (or composition) can be administered in conjunction with other agents, such as antihistamines or immunosuppressants or other immunotherapeutic agents which counteract anti-lysosomal enzyme antibodies. The lysosomal enzyme can be human, recombinant, wild-type or synthetic. Lysosomal enzymes include glucocerebrosidase (for the treatment of Gaucher disease; U.S. Pat. No. 5,879,680, the entire contents of which are incorporated herein by reference, and U.S. Pat. No. 5,236,838, the entire contents of which are incorporated herein by reference), alpha-glucosidase (e.g., acid α-glucosidase) (for the treatment of Pompe disease; WO 00/12740), alpha-galactosidase (e.g., alpha-gal, α-galactosidase or α-gal) (for the treatment of Fabry Disease; U.S. Pat. No. 5,401,650), alpha-n-acetylgalactosaminidase (for the treatment of Schindler Disease; U.S. Pat. No. 5,382,524), acid sphingomyelinase (for the treatment of Niemann-Pick disease; U.S. Pat. No. 5,686,240) and alpha-iduronidase for the treatment of Hurler, Scheie, or Hurler-Scheie disease (WO 93/10244A1). Genes encoding the aforesaid lysosomal enzymes are described in the preceding patent publications as well. The invention also encompasses administration of the functional equivalent of a lysosomal enzyme. A functional equivalent of a lysosomal enzyme is a compound different from the lysosomal enzyme that, when administered to the animal, replaces the function of the lysosomal enzyme to treat the lysosomal storage disorder. Such functional equivalents include, but are not limited to, mutants, analogs and derivatives of lysosomal enzymes.

In one embodiment, (e.g., for treatment of Pompe disease) the lysosomal enzyme is acid alpha-glucosidase, e.g., a precursor form of human acid alpha-glucosidase, such as recombinant human acid alpha-glucosidase produced in Chinese hamster ovary (CHO) cell cultures, can be used (see, e.g., Fuller, M. et al., *Eur. J. Biochem.* 234:903-909 (1995); Van Hove, J. L. K. et al., *Proc. Natl. Acad. Sci. USA* 93:65-70 (1996), the entire teachings of these references are incorporated herein by reference). In another embodiment (e.g., for treatment of Gaucher disease), the lysosomal enzyme is glucocerebrosidase, modified glucocerebrosidase or CEREZYME® enzyme.

The pharmaceutical agent can be administered alone, or in conjunction with the lysosomal enzyme or functional equivalent thereof. The term "in conjunction with," indicates that the pharmaceutical agent is administered at about the same time as the lysosomal enzyme, as described below. The pharmaceutical agent can be administered to the animal as part of a pharmaceutical composition comprising the agent and a pharmaceutically acceptable carrier or excipient and, optionally, one or more additional therapeutic agents. The pharmaceutical agent and lysosomal enzyme can be components of separate pharmaceutical compositions which can be mixed together prior to administration or administered separately.

The pharmaceutical agent can, for example, be administered in a composition containing the lysosomal enzyme, and thereby administered contemporaneously with the lysosomal enzyme. Alternatively, the agent can be administered contemporaneously, without mixing (e.g., by delivery of the pharmaceutical agent on the intravenous line by which the lysosomal enzyme is also administered, or vice versa). In another embodiment, the pharmaceutical agent can be administered separately (e.g., not admixed), but within a short time frame (e.g., within 24 hours) of administration of the lysosomal enzyme.

The preparation of a pharmacological composition that contains active ingredients dissolved or dispersed therein is well understood in the art. Typically such compositions are prepared as injectables either as liquid solutions or suspensions, however, solid forms suitable for solution, or suspensions, in liquid prior to use can also be prepared. Formulation will vary according to the route of administration selected (e.g., solution, emulsion, capsule).

Suitable pharmaceutically acceptable carriers can contain inert ingredients which do not interact with the pharmaceutical agent, lysosomal enzyme and/or additional therapeutic agent. Such carriers include, but are not limited to, sterile water, salt solutions (e.g., NaCl), physiological saline, bacteriostatic saline (saline containing about 0.9% benzyl alcohol), phosphate-buffered saline, Hank's solution, Ringer's-lactate saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, dextrose, lactose, trehalose, maltose or galactose, magnesium stearate, talc, silicic acid, viscous paraffin, perfume oil, fatty acid esters, hydroxymethylcellulose and polyvinyl pyrolidone, as well as combinations thereof. The compositions can, if desired, be mixed with auxiliary agents, e.g., lubricants, preservatives, stabilizers, wetting agents, emulsifiers, salts for influencing osmotic pressure, pH buffers, coloring, flavoring and/or aromatic substances and the like which do not deleteriously react with the active compounds. Additionally, the compositions of the invention may be lyophilized (and then rehydrated) in the presence of such excipients prior to use.

Standard pharmaceutical formulation techniques can be employed, such as those described in Remington's Pharmaceutical Sciences, Mack Publishing Company, Easton, Pa. Methods for encapsulating compositions (such as in a coating of hard gelatin or cyclodextran) are known in the art (Baker, et al., "Controlled Release of Biological Active Agents", John Wiley and Sons, 1986). The composition can be a liquid solution, suspension, emulsion, tablet, pill, capsule, sustained release formulation, or powder. The composition can also be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose or magnesium carbonate. For example, in one embodiment, a composition for intravenous administration typically is a solution in a water-soluble carrier, e.g., sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is administered by injection, an ampule of sterile water for injection or saline can be provided so that the ingredients may be mixed prior to administration.

The pharmaceutical agent can be administered as a neutral compound or as a salt or ester. Pharmaceutically acceptable salts include those formed with free amino groups such as those derived from hydrochloric, phosphoric, acetic, oxalic or tartaric acids, and those formed with free carboxyl groups such as those derived from sodium, potassium, ammonium, calcium, ferric hydroxides, isopropylamine, triethylamine, 2-ethylamino ethanol, histidine, procaine, etc. Salts of compounds containing an amine or other basic group can be obtained, for example, by reacting with a suitable organic or inorganic acid, such as hydrogen chloride, hydrogen bromide, acetic acid, perchloric acid and the like. Compounds with a quaternary ammonium group also contain a counteranion such as chloride, bromide, iodide, acetate, perchlorate and the like. Salts of compounds containing a carboxylic acid or other acidic functional group can be prepared by reacting with a suitable base, for example, a hydroxide base. Salts of acidic functional groups contain a countercation such as sodium or potassium.

Also contemplated within the invention are compositions and kits comprising at least one pharmaceutical agent and at least one lysosomal enzyme, gene or functional equivalent thereof.

The pharmaceutical agent or lysosomal enzyme or gene can be administered by any suitable parenteral or non-parenteral route, including, for example, topically (e.g., cream, ointment), or nasally (e.g., solution, suspension). Parenteral administration can include, for example, intramuscular, intravenous, intraventricular, intraarterial, intrathecal, subcutaneous, or intraperitoneal administration. The agent (e.g. agent, enzyme or nucleic acid) can also be administered orally (e.g., in capsules, suspensions, tablets or dietary), transdermally, intradermally, topically, by inhalation (e.g., intrabronchial, intranasal, oral inhalation or intranasal drops), transmucosally or rectally. Administration can be local or systemic as indicated. More than one route can be used concurrently, if desired. The preferred mode of administration can vary depending upon the particular agent chosen. However, oral, systemic or parenteral administration is generally preferred. In a preferred embodiment, the pharmaceutically agent is administered orally, intramuscularly, intradermally, intravenously or intraperitoneally. In an embodiment, administration is by infusion. For example, the administration can last 0.01-0.1, 0.1-0.5, 0.25, 0.5, 1, 2, or 3 hours.

Delivery can also be by injection into the brain or body cavity of a patient or by use of a timed release or sustained release matrix delivery systems, or by onsite delivery using micelles, gels and liposomes. Nebulizing devices, powder inhalers, and aerosolized solutions are representative of methods that may be used to administer such preparations to the respiratory tract. Delivery can be in vitro, in vivo, or ex vivo. Delivery can be by a number of different ways, including transfection, transformation, gene activation, and electroporation. For example, after contact with the viral vector comprising the lysosomal enzyme or gene, the sample can be returned or readministered to a cell or patient according to methods known to those practiced in the art. In the case of delivery to a patient, such a treatment procedure is sometimes referred to as ex vivo treatment or therapy. Ex vivo gene therapy has been described, for example, in Kasid, et al., *Proc. Natl. Acad. Sci. USA* 87:473 (1990); Rosenberg, et al., *New Engl. J. Med.* 323:570 (1990); Williams, et al., *Nature*

310476 (1984); Dick, et al., *Cell* 42:71 (1985); Keller, et al., *Nature* 318:149 (1985) and Anderson, et al., U.S. Pat. No. 5,399,346 (1994).

The methods of the present invention contemplate single as well as multiple administrations, given either simultaneously or over an extended period of time. The pharmaceutical agent (or composition containing the pharmaceutical agent or enzymes) can be administered at regular intervals, depending on the nature and extent of the lysosomal storage disease's effects, and on an ongoing basis. Administration at a "regular interval," as used herein, indicates that the therapeutically effective amount is administered periodically (as distinguished from a one-time dose). In one embodiment, the lysosomal enzyme is administered periodically, i.e., at a regular interval (e.g., bimonthly, monthly, biweekly, weekly, twice weekly, daily, twice a day or three times or more often a day).

The administration interval for a single individual need not be a fixed interval, but can be varied over time, depending on the needs of the individual. For example, in times of physical illness or stress, if anti-lysosomal enzyme antibodies become present or increase, or if disease symptoms worsen, the interval between doses can be decreased. Depending upon the half-life of the agent in the particular animal or human, the agent can be administered between, for example, once a day or twice monthly.

For example, the administration of the combination therapy (i.e., the lysosomal enzyme and the pharmaceutical agent) can take place once every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 days, or at least once every 1, 2, 3, 4, 5, 6, 7, 8, 9, 10, 11, 12, 13, 14, 15, 16, 17, 18, 19 or 20 weeks, or any combination thereof, using single or divided doses of every 60, 48, 36, 24, 12, 8, 6, 4, or 2 hours, or any combination thereof. Administration can take place at any time of day, for example, in the morning, the afternoon or evening. For instance, the administration can take place in the morning, e.g, between 6:00 a.m. and 12:00 noon; in the afternoon, e.g., after noon and before 6:00 p.m.; or in the evening, e.g., between 6:01 p.m. and midnight. In one embodiment, dexamethasone is administered to the patient in the morning, when suppression of the pituitary adrenal cortex is minimal. In another embodiment, for treatment of Gaucher's disease, the lysosomal enzyme, functional equivalent thereof or gene is administered once every two-three, three-four or two-four weeks. In another embodiment, for treatment of Pompe disease, the lysosomal enzyme, functional equivalent thereof or gene is administered once every one-two, two-three, three-four or four-five weeks. The pharmaceutical agent can be administered before, during or after the onset of skeletal complications or pathology.

The pharmaceutical agent can be administered prior to, or concurrently with, or shortly thereafter, the lysosomal enzyme, functional equivalent thereof or gene. The pharmaceutical agent should be administered sufficiently prior to administration of the enzyme so as to permit modulation (e.g., up-regulation) of the target cell surface receptors to occur. For example, in one preferred embodiment, the pharmaceutical agent is administered at least two-three, three-four or four-five days before the lysosomal enzyme is administered. In another preferred embodiment, the pharmaceutical agent is administered at least three days before the lysosomal enzyme is administered. In another preferred embodiment, the pharmaceutical agent is administered more than three days before the lysosomal enzyme is administered. In one embodiment, to treat Gaucher disease, a pharmaceutical agent such as dexamethasone is administered to a patient at least 2-3 days prior to administration of CEREZYME® enzyme, modified glucocerebrosidase or a functional equivalent thereof. For example, the dexamethasone can be administered twice a day (e.g., once in the morning and once in the late afternoon or evening) for two days, beginning either two or three days prior to treatment with the lysosomal enzyme. In another embodiment, to treat Pompe disease, a pharmaceutical agent such as insulin can be administered to a patient or 0.25, 0.5, 1, 2, 3, 4, 5, 6, 7, 8, 9, 10, 11 or 12 hours, or 1, 2, 3, 4, 5, 6, 7, 8 days, prior to administration of acid alpha-glucosidase enzyme, modified acid alpha-glucosidase or a functional equivalent thereof. In one embodiment, insulin is administered to the patient before the enzyme is administered to the patient. Moreover, in the methods described herein, more than one pharmaceutical agent can be administered to the patient. For example, glucose can be administered to a patient prior to, or concurrently with, or shortly after, insulin in order to counteract an undesired effect of insulin administration, for example, to prevent or reduce hypoglycemia.

The pharmaceutical agent, lysosomal enzyme or functional equivalent thereof or gene can be administered in a dosage of, for example, 0.1 to 100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day for example, the dosage can be 0.1-0.5 mg/kg, 0.5-2 mg/kg, or 0.01-2.4 g mg/kg. Dosage forms (composition) suitable for internal administration generally contain from about 0.1 milligram to about 500 milligrams of active ingredient per unit. In these pharmaceutical compositions the active ingredient will ordinarily be present in an amount of about 0.5-95% by weight based on the total weight of the composition.

The pharmaceutical agent or lysosomal enzyme or functional equivalent thereof or gene can be administered in an "effective amount" (i.e., a dosage amount that, when administered at regular intervals, is sufficient to treat the disease, such as by ameliorating symptoms associated with the disease, preventing or delaying the onset of the disease, and/or also lessening the severity or frequency of symptoms of the particular lysosomal enzyme disease, as described above). Thus, an effective amount of the agents or compositions of the invention is a quantity which will result in a therapeutic or prophylactic benefit for the animal. The effective amount will vary, depending on such factors as the route of administration, the condition of the patient, the nature and extent of the disease's effects, and the like. Such factors are capable of determination by those skilled in the art.

As used herein, the term "effective amount" also means the total amount of each active component of the composition or method that is sufficient to show a meaningful patient benefit, i.e., treatment, healing, prevention or amelioration of the relevant medical condition, or an increase in rate of treatment, healing, prevention or amelioration of such conditions. For example, an effective amount of a pharmaceutical agent is an amount sufficient to achieve a desired therapeutic and/or prophylactic effect, such as an amount sufficient to modulate lysosomal enzyme receptors or their activity, e.g., to thereby treat a lysosomal storage disease or symptom thereof. When applied to a combination, the term refers to combined amounts of the active ingredients that result in the therapeutic effect, whether administered in combination, serially or simultaneously.

The amount of pharmaceutical agent, lysosomal enzyme or functional equivalent thereof or nucleic acid administered to the individual will depend on the characteristics of the individual, such as general health, age, sex, body weight and tolerance to drugs as well as the degree, severity and type of rejection. The skilled artisan will be able to determine appropriate dosages depending on these and other factors using standard clinical techniques.

In addition, in vitro or in vivo assays may optionally be employed to help to identify optimal dosage ranges. The precise dose to be employed will also depend on the route of administration, the seriousness of the disease, and the individual's circumstances. Effective doses may be extrapolated from dose-response curves derived from in vitro or animal model test systems. The amount of an agent of the present invention will also depend on the disease state or condition being treated along with the above clinical factors and the route of administration of the compound. For example, in times of physical illness or stress, or if anti-lysosomal enzyme antibodies become present or increase, or if disease symptoms worsen, the amount can be increased.

For treating humans or animals, about 1 mg/kg of body weight to about 20 mg/kg of body weight of the enzyme can be administered. In a preferred embodiment, the effective amount of agent or lysosomal enzyme is about 1-10 mg enzyme/kg body weight of the individual. In another embodiment, the effective amount of agent or lysosomal enzyme is about 1-5 mg enzyme/kg body weight of the individual. In another embodiment, the effective amount of CEREZYME® enzyme is 2-5 mg/kg (e.g., 2.5 mg/kg of body weight). For example, initial dosages can range from 2.5 U/kg 3 times a week to 60 U/kg once every two weeks. In another embodiment, the effective amount of lysosomal enzyme for treatment of Pompe disease is at least 10 mg/kg of body weight. The effective amount for a particular individual can be varied (e.g., increased or decreased) over time, depending on the needs of the individual.

The term "unit dose" when used in reference to a therapeutic composition of the present invention refers to a physically discrete unit suitable as unitary dosage for the subject, each unit containing a predetermined quantity of active material calculated to produce the desired therapeutic effect in association with the required diluent; i.e., carrier or vehicle. In addition to the ingredients particularly mentioned above, the formulations of the present invention may include other agents conventional in the art having regard to the type of formulation in question.

While this invention has been particularly shown and described with references to preferred embodiments thereof, it will be understood by those skilled in the art that various changes in form and details may be made therein without departing from the scope of the invention encompassed by the appended claims.

The teachings of all references cited herein are incorporated in their entirety, including the references cited above and the following references.

1. Kornmfield, S. and Mellman, I., *Annual Review Cell Biology*, 5:483-525 (1989).
2. Friedman, B., et al., *Blood*, 93:2807-2816 (1999).
3. Clairmont, K. B., Czech, M. P., *Endocrinology*, 127(4): 1568-1573 (1990).
4. Zhou, M., et al., *American Journal of Physiology (Endocrinology Metabolism*, 38), E187-E196 (1998).
5. Villevalois-Cam, L., et al., *Journal of Cellular Biochemistry*, 77:310-322 (2000).
6. Kandror, K. V., and Pilch, P. F., *Journal of Biological Chemistry* 271(36):21703-21708(1996).
7. Zhang, Q., et al., *Journal of Biological Chemistry*, 272(38): 23703-21706 (1997).
8. Brulke, T., et al., *European Journal of Biochemistry*, (1990).
9. Hu, K., et al., *Journal of Biological Chemistry*, 265(23): 13864-13870 (1990).
10. Brulke, T., et al., *Journal of Biological Chemistry*, 265 (12):6650-6655 (1990).
11. Brulke, T., et al., *EMBO Journal*, 8:681-686 (1989).
12. Cowan, H. B., et al., *Archives of Biochemistry and Biophysics*, 296:314-320 (1992).
13. Montaner, L. J., et al., *The Journal of Immunology*, 162: 4606-4613 (1999).
14. Stein, M., et al., *Journal of Experimental Medicine*, 176: 287-292 (1992).
15. Mokoena, T., Gordon, S., *Journal of Clinical Investigation*, 75:624-631 (1985).
16. Schreiber, S., et al., *The Journal of Immunology*, 151(9): 4973-4981 (1993).
17. Treichel, U., et al., *Journal of Cellular Physiology*, 158: 527-534 (1994).
18. Sato, Y. and Beutler, E. *Journal of Clinical Investigation*, 91: 1909-1917 (1993).
19. Harris, N. et al., *Blood*, 80: 2363-2373 (1192).
20. Brain, J. D. and Frank, N. R. *Journal of Applied Physiology*, 25: 63-69 (1968).

EXAMPLE 1

Dexamethasone Increases Uptake of CEREZYME® Enzyme by Liver Macrophage Cells In Vitro Three representative cell types of the liver were assayed for CEREZYME® enzyme uptake under the influence of dexamethasone. An alveolar macrophage cell line was used to represent liver Kupffer cells, Hep3B cells were used to represent hepatocytes and liver sinusoidal endothelial cells (LSECs) were primary cells derived from the human liver.

The rat alveolar macrophage cell line NR 8383 (ATCC# CRL-2192) were cultured in Kaighn's modified F12K nutrient mixture (Gibco# 21127-002) with 2 mM L-glutamine (Gibco# 25030-081), 15% heat-inactivated fetal bovine serum (FBS) (Gibco# 16000-044) and 1× penicillin/streptomycin. Most of the cells were attached to the dish, with some in suspension. Hep3B cells were grown in MEM-eagle (Gibco# 11960-044) with Earles salts and 10% FBS, 1× nonessential amino acid (NEAA), 1× sodium pyruvate and 1× penicillin/streptomycin. Human liver sinusoidal endothelial cells (LSECS) (ACBRI#-566) were purchased from Applied Cell Biology Research Institute through Cell Systems, Inc. Cells were cultured in CS-C Media (CSC# 4Z0-500) with additional 10% FBS. During passage, the culture dishes or flasks were treated with attachment factor solution (CSC# 4Z0-210). Prior to seeding, the purity of the LSECs was confirmed by immunostaining with anti-VOA Willebrand factor (data not shown).

For dexamethasone or other drug treatment, the cells were incubated with the drugs under various conditions as indicated in each figure legend (FIGS. 1A-F). For two-day treatments, a new batch of each drug was added on the second day. On the third day, CEREZYME® enzyme uptake assays were performed. Briefly, macrophage cells were collected from culture flasks by phosphate buffer saline (PBS) wash. After the cells were washed with Kaghan's media without FBS, the cells were resuspended in uptake media (Kaghan's media with 4 mg/ml BSA (Sigma# A-7030) and 25 mM hepes at pH 6.8) at $1\times10^6$ cells per milliliter. One milliliter of cell aliquot was distributed into 1.5 ml microcentrifuge tubes in duplicate. Yeast mannan (Sigma# M-7504) in deionized water, if required, was added to a final concentration of 2 mg/ml to inhibit the mannose receptor-mediated CEREZYME® enzyme uptake. CEREZYME® enzyme at 1 U/ml was added to the tubes as indicated. The cells were incubated for uptake at 37° C. for 2 hours with periodic mixing every 15 minutes. After uptake, the cells were pelleted at 1000×g for 3 minutes in a microcentrifuge and washed twice with 1 ml of ice-cold PBS containing 1 mg/ml of yeast mannan and twice with PBS. Cell pellets were dissolved in 1 ml of KP buffer (50 mM potassium phosphate, 0.25% Triton X-100), pH 6.5, with COMPLETE™ protease inhibitors (Roche# 1687498).

For CEREZYME® enzyme uptake by Hep 3B cells and liver sinusoidal endothelial cells, the overall procedures were similar to the protocol as described for macrophages except that these cells were attached. Cells were grown in 6-well plates and the uptake media was DMEM with 4 mg/ml BSA and 25 mM hepes at pH 6.8. 1.5 ml of uptake media was used for each well. After washing the wells twice with PBS plus 1 mg/ml yeast mannan and twice with PBS, the cells were lysed in 1 ml KP buffer as for the macrophages.

The lysates were used for glucocerebrosidase assay in duplicate or triplicate with 4-MU-beta-glucoside (Sigma# M-3633) as substrate and with CEREZYME® enzyme as standard. Proteins were quantified using a MicroBCA protein assay kit (Pierce) with BSA as standard. The β-glucocerebrosidase activity was also normalized to the control sample that was set at 100%.

Figure 1A:
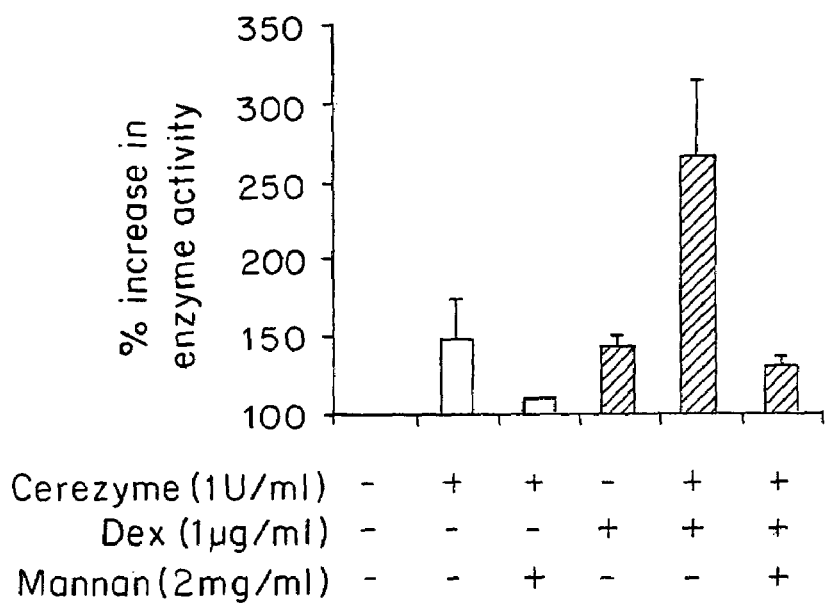
FIG. 1A depicts the increase of CEREZYME® enzyme uptake by dexamethasone-pretreated rat alveolar macrophage cells as a function of percent increase in enzyme activity. Values were normalized to endogenous glucocerebrosidase activity, which was set at 100%.
Figure 1B:
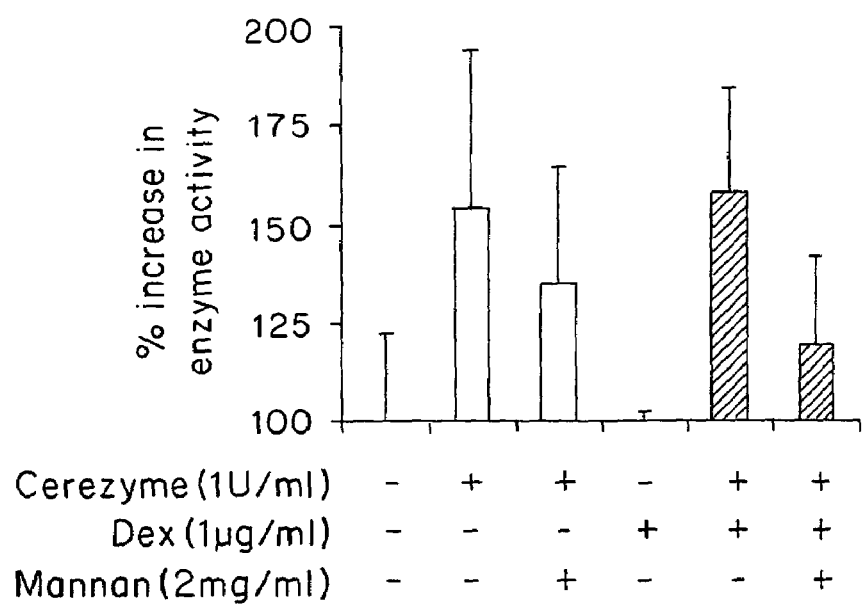
FIG. 1B depicts CEREZYME® enzyme uptake by dexamethasone-pretreated liver sinusoidal endothelial cells as a function of percent increase in enzyme activity. Values were normalized to endogenous glucocerebrosidase activity, which was set at 100%.
Figure 1C:
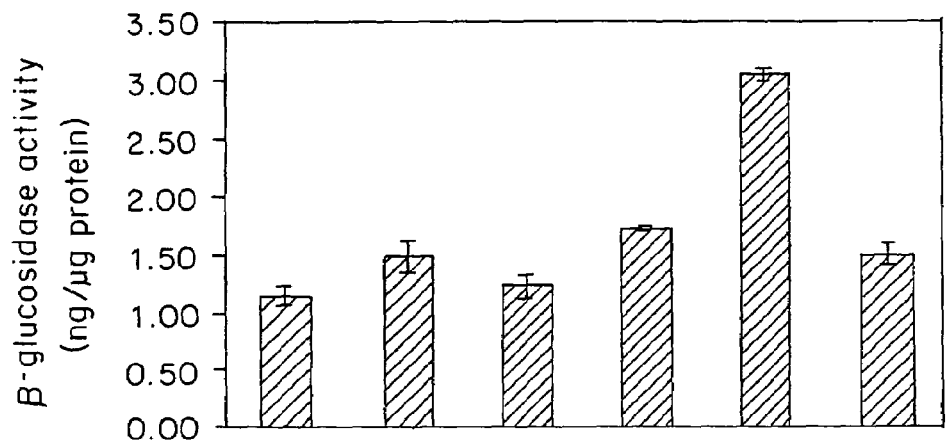
FIG. 1C depicts the increase of CEREZYME® enzyme uptake by dexamethasone-treated rat alveolar macrophage cells as a function of β-glucosidase enzyme activity (ng/ug protein).
Figure 1D:
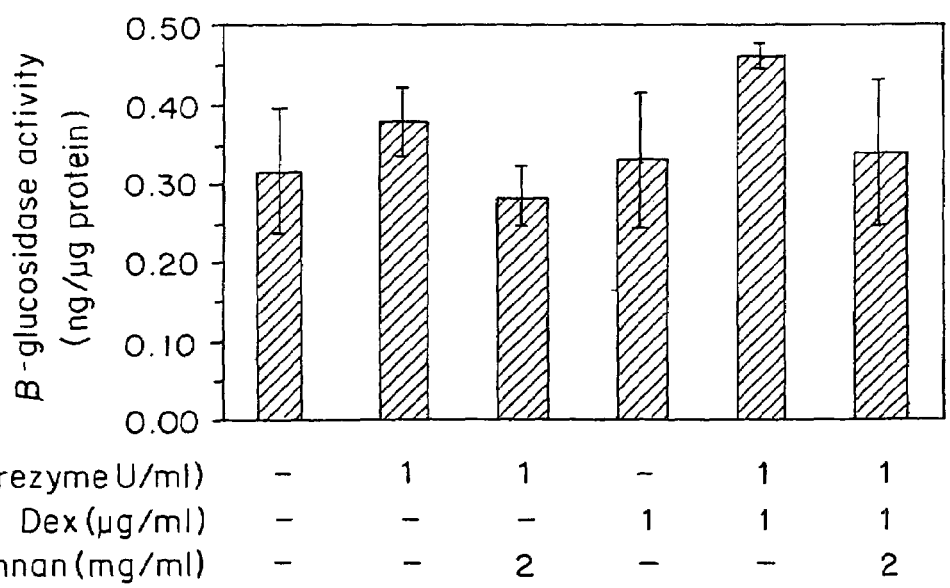
FIG. 1D depicts CEREZYME® enzyme uptake by dexamethasone-treated liver sinusoidal endothelial cells as a function of β-glucosidase enzyme activity (ng/ug protein).
Figure 1E:
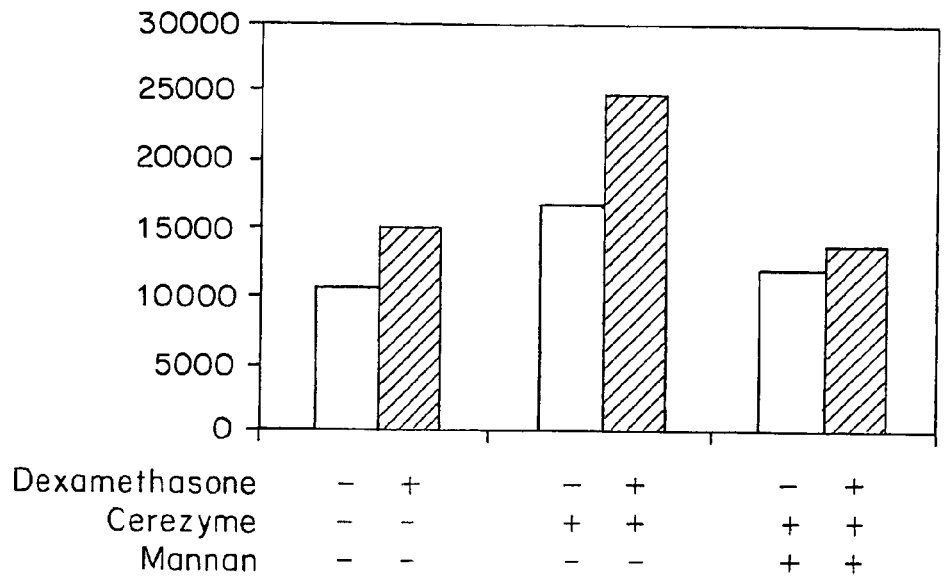
FIG. 1E depicts increase of uptake of CEREZYME® enzyme by dexamethasone-treated rat alveolar macrophage cells. The left bar in each group represents the "control" cells that had not been treated with dexamethasone. The right bar in each group represents cells that had been treated with dexamethasone. The first group represents cells that did not receive CEREZYME® enzyme. The second group represents cells that did receive CEREZYME® enzyme. The third group represent cells that received CEREZYME® enzyme and a mannose receptor inhibitor (yeast mannan).
Figure 1F:
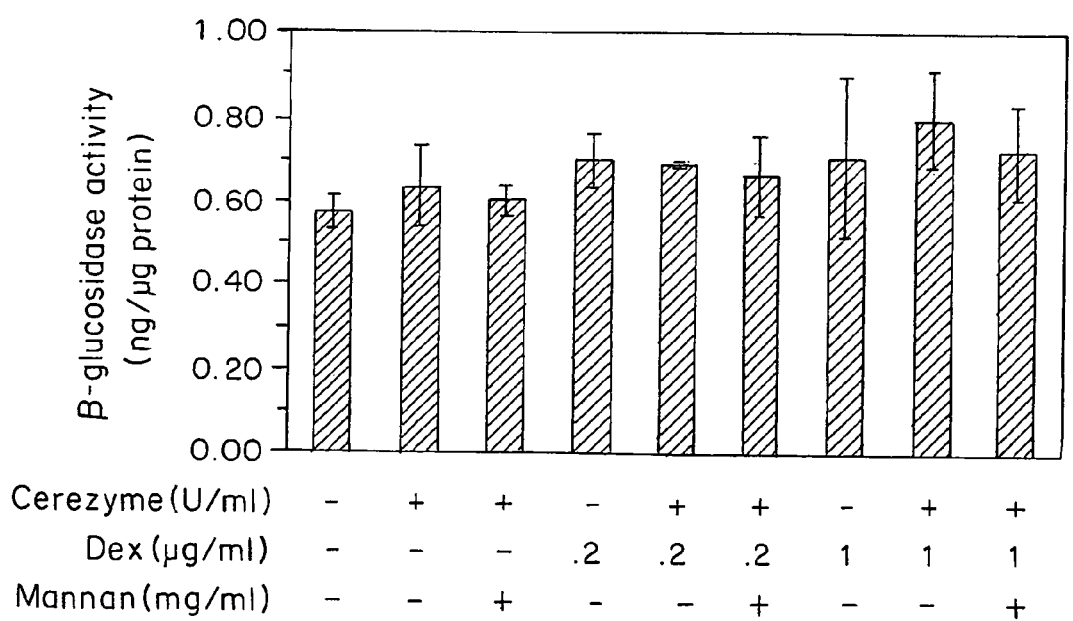
FIG. 1F depicts CEREZYME® enzyme uptake by dexamethasone-treated hepatocytes.

As shown in FIGS. 1A and 1B, both the macrophage cells and the liver sinusoidal endothelial cells avidly took up CEREZYME® enzyme (second bar in each graph). This uptake could be nearly completely inhibited by yeast mannan (third bar, FIG. 1A) to the endogenous level of glucocerebrosidase activity in macrophages (first bar, FIG. 1A) and partially inhibited for LSECs (FIG. 1B). These results suggest that the macrophage uptake of CEREZYME® enzyme is almost completely mediated by the mannose receptor, whereas for the LSECs, other receptors that bind terminal mannose may also contribute to CEREZYME® enzyme uptake. It has been reported that the LSECs may have receptors that can bind terminal mannose with lower affinity (Sato, 1993 #19), which could account for the mannan resistant uptake (FIG. 1B, third bar). After dexamethasone pretreatment, CEREZYME® enzyme uptake by macrophage cells was increased by about 3-fold compared to non-treated cells (FIG. 1A). This enhanced uptake of CEREZYME™ enzyme by dexamethasone-pretreated macrophages was likely the result of the increased expression of the mannose receptor (Cowan, 1992 #21), since the uptake was completely inhibited by yeast mannan. This increased uptake phenomenon was not observed for the liver sinusoidal endothelial cells (FIG. 1B, indicating that dexamethasone has differential effects on these two cell types. FIGS. 1C and 1D indicate similar data, presented as β-glucosidase activity (ng/ug protein). As indicated in Figure C, the dexamethasone-treated macrophage cells enhanced CEREZYME® enzyme uptake by about 5-fold compared to non-treated cells (fifth bar vs second bar after subtracting the mannan-inhibited values). The hepatocytes, in contrast to the macrophages and endothelial cells, barely took up any CEREZYME® enzyme (FIG. 1F), whether or not they were treated with dexamethasone. This is consistent with the fact that the hepatocytes do not express the mannose receptor.

The stimulative effect of dexamethasone on CEREZYME® enzyme uptake by macrophages was time dependent. A minimal two-day treatment was required to bring out the effect, whereas one-day treatment was with minimal effect (FIG. 2). This observation correlated well with the fact that the increased expression of mannose receptor on macrophage cells by dexamethasone involves de novo transcription of its messenger RNA and protein synthesis (Cowan, 1992 #21).

Interferon-γ has been shown to down-regulate the mannose receptor expression on macrophage cells (Harris, 1992 #17). However, the interferon-γ effect is species specific; for example, mouse interferon-γ will not act on macrophages of other species. Therefore, the species specificity of dexamethasone's effects was tested by including mouse interferon-γ, which should not have any effect on rat macrophage cells. This was indeed the case. Mouse interferon-γ did not enhance or inhibit CEREZYME® uptake by rat macrophage cells, whereas dexamethasone did enhance uptake (FIG. 2), suggesting that the effects of dexamethasone on macrophage cells are not species-specific.

EXAMPLE 2

Dexamethasone Pretreatment Increases Uptake of CEREZYME® Enzyme by Tissue Macrophage Cells In Vivo To assess the effect of dexamethasone treatment on CEREZYME® enzyme uptake by liver macrophage (Kupffer cells) in vivo, Fisher rats (female, ~130 g) were divided into four groups (n=3). The first and second groups of rats only received vehicle PBS without dexamethasone, and the third and fourth groups were treated with water-soluble dexamethasone sodium phosphate (American Reagent Laboratories Inc.) at 10 μg and 100 μg (diluted into 200 μl PBS) per rat through intraperitoneal injection. Four doses of dexamethasone were given over two consecutive days, one dose in early morning and one dose in late afternoon on each day. On the third day, CEREZYME® enzyme at 2.5 U per rat (~18 U/kg) diluted in PBS was administrated into the second, third and fourth groups of rats through tail vein bolus injection. The first group was used as negative control.

Two hours after CEREZYME® enzyme injection, the rats were euthanized and livers were dissected and fixed in 2% paraformaldehyde (Electron Microscopy Sciences, EMS #15710-S) plus 0.01% glutaraldehyde (EMS #-16210) in PBS for 1 hour at room temperature. The fixatives were then replaced overnight with ice-cold 30% sucrose solution in water at 4° C. The tissues were embedded in tissue-freezing OCT compound (EMS # 62550-12) and thin-sectioned at 5 μm.

CEREZYME® enzyme uptake in these rat livers was assessed by indirect immunofluorescence microscopy. Liver sections were analyzed for the presence of macrophages (CD11b, Serotech) and human glucocerebrosidase (1B5) by co-staining. Species-specific anti-human glucocerebrosidase antibody, which does not recognize the endogenous rat enzyme, was used to label the CEREZYME® enzyme taken up by liver cells after CEREZYME® enzyme infusion. An anti-macrophage antibody was used to co-stain the Kupffer cells. There was a clear trend that dexamethasone pretreatment enhanced CEREZYME® enzyme uptake by Kupffer cells in the liver. More Kupffer cells were labeled with anti-human glucocerebrosidase antibody in the dexamethasone-treated rat liver sections than in the untreated sections (data not shown).

Direct measurement of glucocerebrosidase activity in spleen, liver and bone marrow tissues after CEREZYME® enzyme uptake was also assessed in another set of experiments. Five groups of rats were used (n=3). The first four groups were treated in the same manner as described above, whereas the fifth group of rats was not treated with dexamethasone but received 10 U of CEREZYME® enzyme per rat and used as positive controls. Tissue of spleen and liver were obtained and homogenized in KP buffer, at 100 mg of wet tissue per ml buffer with protease inhibitors. The homogenate were centrifuged at 14000×g for 15 minutes at 4° C. The supernatants were saved and measured for glucocerebrosidase activity and normalized to protein content as described above.

The total glucocerebrosidase activity in spleens of rats treated with 100 µg dexamethasone and receiving 2.5 U of CEREZYME® enzyme was increased to the level of non-treated rats receiving 10 U of CEREZYME® enzyme, an overall 4-fold increase (FIG. 3, lower panel). Since the other cell types in the spleen do not have mannose receptors, this indicates that it is the enhanced uptake of CEREZYME® enzyme by the dexamethasone-treated macrophages that contributes to the increased total glucocerebrosidase activity in the spleen. The results from bone marrow cells, obtained from femur bones of the rats, however, did not reveal any stimulative effects of dexamethasone (FIG. 3, upper panel).

Quantitative analysis of the dexamethasone effects on CEREZYME® enzyme uptake in vivo was performed on macrophage cells isolated from spleens through the attachment method (Gessani S, 2000 #35). Fisher rats (female, 180-200 g) were used and divided into four groups. After dexamethasone (50 µg/rat) pretreatment and CEREZYME® enzyme (or unmodified glucocerebrosidase) injection, rat spleens were excised and cut into small pieces. The total spleen cells were released by pressing between two frosted cover slides, followed by washing with 15 ml of RPMI media containing 10% heat-inactivated FBS. Red blood cells were lysed with red blood cell lysis buffer (Sigma). The rest of the splenocytes were seeded in 150-mm tissue culture dishes and incubated at 37° C. for 1 hour for the attachment isolation of macrophages. 15 ml of media were added to five 150-mm tissue culture dishes as blanks for nonspecific protein binding. After removing the cells in suspension and washing the attached cells 5 times with PBS, the attached cells were lysed in KP buffer by scrapping and assayed for glucocerebrosidase activity and protein content. The average of protein content of the blank dishes was subtracted from each cell sample. For dose response of CEREZYME® enzyme to dexamethasone, rats pretreated with dexamethasone were injected with different doses of CEREZYME® enzyme as for the control groups without dexamethasone pretreatment. Attached cells (>90% spleen macrophages) were isolated for glucocerebrosidase assay as described above. As shown in FIG. 4A, spleen macrophages isolated from rats pretreated with dexamethasone who received 18 U/kg of CEREZYME® enzyme had much higher activity than macrophage cells isolated from non-treated control rats who received 18 U/kg of CEREZYME® enzyme. The activity was also higher than that of the non-treated rats who received 72 U/kg of CEREZYME® enzyme, suggesting that at least 3-fold increase in CEREZYME® enzyme uptake can be achieved in vivo by dexamethasone pretreatment after normalizing the dose contribution. The absolute enzyme activity, however, was ~220% of the control without dexamethasone treatment (FIG. 4A). The dexamethasone effects were also tested at other CEREZYME® enzyme doses at 7 U/kg and 72 U/kg respectively, which are either below or above the saturation levels (Mistry, 1996 #10). As is shown in FIG. 4B, at both doses, the dexamethasone effects were about the same and increased CEREZYME® enzyme uptake to a similar level as with 18 U/kg of CEREZYME® enzyme, namely, about 3-fold increase after dosage correction. The absolute CEREZYME® enzyme activity was ~250% of the control sample at 72 U/kg.

Finally, unmodified recombinant glucocerebrosidase was also assessed for uptake under the influence of dexamethasone. Spleen macrophages were isolated from control and dexamethasone-treated rats injected with or without unmodified glucocerebrosidase by the attachment method. Attached cells (>90% macrophages) were assayed for glucocerebrosidase activity as described in Example 2, FIGS. 4A and 4B. Interestingly, an effect similar to that for the carbohydrate-remodeled CEREZYME® enzyme was found (FIG. 5). This was quite likely as the unmodified glucocerebrosidase has one high mannose oligosaccharide chain (data not shown) that can bind mannose receptor on macrophages the same way as the core mannose oligosaccharide chains on CEREZYME® enzyme do.

To determine if receptor up-regulation will also occur in diseased macrophage cells in vivo, lung alveolar macrophages that were known to have large amounts of sphingomyelin lipid accumulation were isolated from 4 month-old acid sphingomyelinase (ASM) knockout mice that were pretreated with dexamethasone for 3 consecutive days, according to the protocol of Brain and Frank (Brain, 1968 #34). Alveolar macrophages filled with lipids isolated from non-treated mice were used as control. Cells were seeded into 12-well plates and incubated at 37° C. for 1 hour for attachment. CEREZYME® enzyme uptake and enzyme assays were performed as for the liver cells. As shown in FIG. 6, the lung alveolar macrophage cells pretreated with dexamethasone had a much stronger uptake of CEREZYME® enzyme than the macrophage cells from non-treated ASM knockout control mice, suggesting that the lipid accumulation in the lysosomes of macrophages does not affect their response to dexamethasone treatment.

EXAMPLE 3

Insulin/Glucose Increases Alpha-galactosidase Uptake by Cells In Vitro

Muscles are the major target tissues for enzyme replacement therapy of Pompe disease due to the lack of acid alpha-glucosidase. To determine if the M6P/IGF-II receptor-mediated lysosomal enzyme uptake pathway can be augmented by insulin/glucose, the effects of insulin/glucose were analyzed on induced muscle cells (myotubes) in vitro. L6 myoblasts (or induced myotubes) and Hep3B cells were cultured in 6-well dishes. Rat L6 myoblasts (ATCC# CRL-1458) were cultured at 37° C. under 5% $CO_2$ in VitaCell DMEM media (ATCC# 30-2002) with 4 mM L-glutamine, 10% fetal bovine serum (Gibco #16000-044) and 1× penicillin/streptomycin. Once confluent, cells were switched to VitaCell DMEM plus 2% horse sera (Gibco# 26050-088) and 1× penicillin/streptomycin. Media were changed every 3 days and at day 9-10, myotubes could be observed as multinuclear tubes. About 30-40% of the myoblasts formed myotubes. Cells were used for uptake assay at day 10. Hep3B cells were grown in MEM-eagle (Gibco# 11960-044) with 10% FBS, 1×NEAA, 1× sodium pyruvate and 1× penicillin/streptomycin.

Before the uptake assay, the cells were washed once with PBS and once with DMEM minus glucose media (Gibco#11966-025), then the cells were starved in 1.5 ml of DMEM minus glucose media for 1 hour at 37° C. After starvation, the cells were switched to uptake media (DMEM with or without glucose, plus 4 mg/ml BSA, 2.5 mM beta-glycerophosphate (Sigma #G-6376), 25 mM Hepes, pH 6.8. Insulin (Calbiochem, #40769), M6P (Sigma # M-6876) and 2 µg/ml recombinant human alpha-galactosidase (as a model protein because of its better M6P phosphylation) were added as indicated in FIGS. 7A and 7B. Uptake of enzyme was continued for 4 hours at 37° C. After uptake, the cells were washed twice with PBS containing 1 mM M6P and once with PBS, then lysed in alpha-galactosidase assay buffer (50 mM sodium citrate, pH 6.8) plus 1% Triton X-100 and protease inhibitors. The lysates were assay for alpha-galactosidase activity with 4-MU-galactoside (Sigma #M-7633) as substrate and normalized to protein content.

As shown in FIGS. 7A and 7B, treatment of muscle cells (myotubes) with insulin/glucose during the uptake period increased alpha-galactosidase uptake (second and third bar pairs) compared to starved cells without insulin/glucose stimulation (first bar pair). In FIG. 7A, the increase was approximately 200% of control. In FIG. 7B, the increase was 200-300% of control. These results are approximate to the theoretical value of 2-3-fold increase in recycling of the endosomal pool of M6P/IGF-II receptor to the cell surface after insulin/glucose stimulation (see Clairmont et al., *Endocrinology*, 127(4):1568-1573 (1990)). The entire alpha-galactosidase uptake can be inhibited by the presence of 5 mM M6P (second (hatched) bar in each pair) to the endogenous level (last (open) bar), indicating the uptake is solely dependent on the M6P/IGF-II receptor-mediated endocytosis.

Hepatocytes and fibroblasts were also tested for insulin/glucose stimulation of uptake of alpha-galactosidase as described in Example 2. As shown in FIG. 8, insulin/glucose also enhanced alpha-galactosidase uptake in hepatocytes by approximately 2-fold (third bar group) compared to starved cells without insulin/glucose (first bar). Glucose alone resulted in less stimulation than glucose/insulin (second bar).

Figure 9:
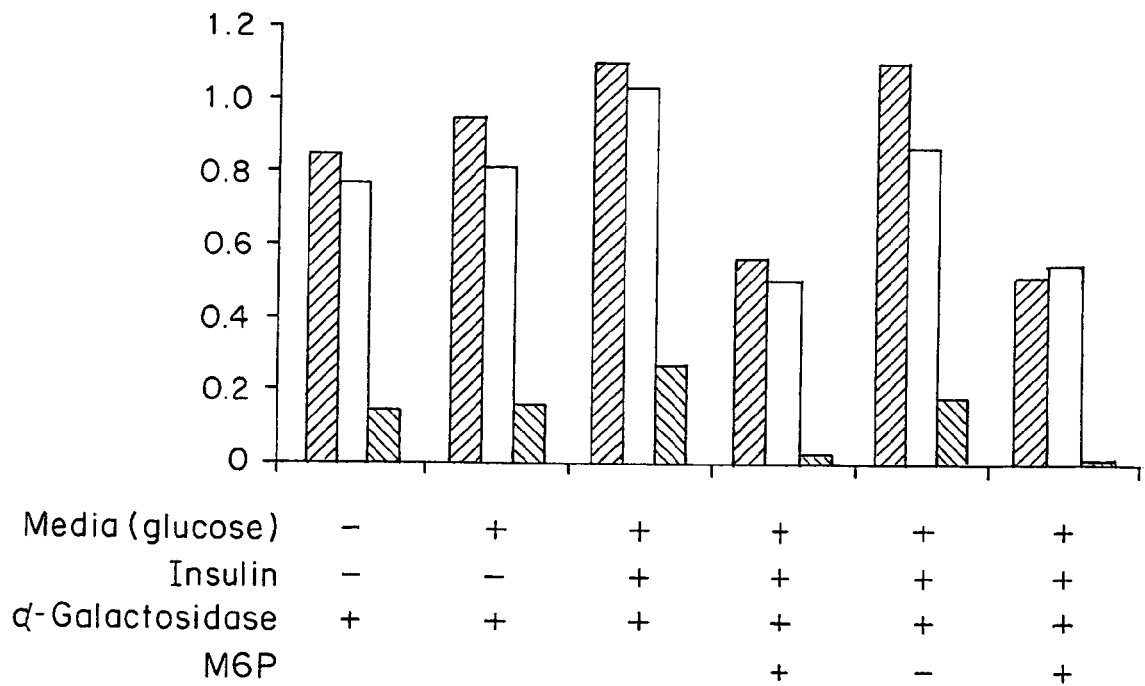
FIG. 9 depicts the increase of alpha-galactosidase uptake by normal, insulin/glucose-treated fibroblast, fabry fibroblast and Hep 3B cells. The grey bar represents Hep 3B cells, the black bar represents normal fibroblast cells and the white bar represents Fabry fibroblast cells.

Human skin fibroblasts (ATCC# CRL-1502) were grown at 37° C. under 5% $CO_2$ in MEM with Earle's balanced salts, 2× essential and non-essential amino acids (NEAA) (Gibco# 11130-051, 11140-050) and vitamin (Gibco# 1120-052), 20% fetal bovine serum (Gibco# 16000-044, not heat-inactivated) plus 1× penicillin/streptomycin. The pH of the media was adjusted to approximately 7 with sodium bicarbonate (Gibco #25080-094). As indicated in FIG. 9, treatment with insulin/glucose increased α-gal uptake in hepatocytes and fibroblasts.

Different cell lines corresponding to target tissues can be tested for insulin/glucose effects on uptake of enzymes in vitro by cell culture. This can give guidance as to which target tissue will have the most benefit through this approach. Insulin's effects on asialoglycoprotein receptors and mannose receptors can also be evaluated. If they are down-regulated, then the overall efficacy of insulin/glucose in combination with ERT and gene therapy will be even greater. If M6P/IGF-II receptors on hepatocytes and liver sinusoidal endothelial cells are also up-regulated, then a physiological concentration of insulin can be evaluated in animal models. Under this condition, it is expected that only muscle and fat tissues should respond to insulin and the M6P/IGF-II cell surface density increased.

EXAMPLE 4

Insulin-Glucose Increases the Muscle Uptake of Alpha-galactosidase In Vivo

To directly evaluate the effects of insulin/glucose on alpha-galactosidase uptake in vivo, normal (129 SV, 3-4 month, male) and Fabry mice (on 129SV background, 3-4 month, male) were used for uptake assays under different conditions.

Normal mice were fasted overnight from 5 p.m. to 9 a.m. next morning, and then divided into three groups. The first group did not receive alpha-galactosidase injection and served as the normal naïve control. The second group directly received alpha-galactosidase injection (6 mg/kg) through tail vein as bolus injection; the third group was first gavaged with 0.5 ml of 50% glucose followed by subcutaneous injection of insulin (0.25 U) on the upper back 10 minutes later, after another 45 minutes, alpha-galactosidase was injected as for the second group. Two hours after alpha-galactosidase injection, different tissues (heart, diaphragm, tongue, muscle gastrocnemius, muscle vastus laterus, muscle paraspinal) were collected and assayed for alpha-galactosidase activity after homogenization in alpha-galactosidase assay buffer plus 1% of triton and 1× protease inhibitor cocktail. As shown in FIG. 10, the first bar in each panel shows the endogeneous alpha-galactosidase activity of the naïve animal tissues. Alpha-galactosidase injection alone increased its activity in all the muscle tissues of the second group (second bar in each panel), indicating that the injected recombinant alpha-galactosidase was taken up by different muscles in vivo. As expected, insulin/glucose pretreatment enhanced the uptake of alpha-galactosidase into muscle tissues, with the skeletal muscles being most stimulated by 2-3 fold (third bar in upper panels); for the heart and diaphragm, the stimulation of uptake was also obvious (lower panels).

Similar results were also obtained from Fabry mice. Here, 4 groups of Fabry mice were used and similarly treated as for the normal mice. The first group was used as Fabry naïve control without alpha-galactosidase injection; the second group was the normal mice naïve control to serve for the endogenous activity in normal animal tissues, which was set at 100%; the third group received alpha-galactosidase injection without insulin/glucose treatment; the fourth group received glucose gavage (1 ml) before alpha-galactosidase injection without extra insulin to see if the physiological response to food intake will elicit insulin secretion that up-regulates M6P/IGF II receptor and stimulates alpha-galactosidase uptake; the last group received both insulin and glucose before alpha-galactosidase injection. As shown in FIG. 11, the first group did not have any alpha-galactosidase activity in any tissue as expected for Fabry mice. The second group (bar) only served as wildtype controls that were set at 100%. For the third group, there were about similar levels of alpha-galactosidase activity in all of the tissues as the wildtype tissues except for the heart which has more than 10-fold increase in alpha-galactosidase activity over the wildtype tissue. Glucose alone in the fourth group could indeed stimulate alpha-galactosidase uptake and doubled the activity in the heart and diaphragm (low panels), with less stimulation in the skeletal muscles (upper panels). The reason for the better stimulation in alpha-galactosidase uptake into the heart and diaphragm is unclear; it is quite likely that these two organs are more sensitive to physiological levels of insulin after food intake. Glucose combined with insulin gave the best stimulation for alpha-galactosidase uptake into skeletal muscles (upper panels), suggesting such strategy can increase M6P-bearing lysosomal enzyme uptake into skeletal muscles.

What is claimed is:

1. A method of treating Gaucher disease in a patient in need thereof, comprising administering to the patient an effective amount of:
   a) a glucocorticoid steroid that increases the surface density of mannose receptors on macrophages; and
   b) imiglucerase, a recombinantly produced carbohydrate-modified glucocerebrosidase;
   wherein the glucocorticoid steroid is administered at a time sufficiently prior to administration of the imiglucerase to permit an increase in the surface density of mannose receptors on macrophages in the patient prior to exposure of the macrophages to said imiglucerase.

2. The method of claim 1, wherein the glucocorticoid steroid is dexamethasone.

3. A method of increasing uptake of imiglucerase, a recombinantly produced carbohydrate-modified glucocerebrosidase, by a macrophage, comprising exposing the macrophage to a glucocorticoid steroid that increases the surface density of mannose receptors on macrophages at a time sufficiently prior to exposing the macrophage to the imiglucerase to permit an increase in the surface density of mannose receptors on the macrophage prior to exposure of the macrophage to the imiglucerase.

4. The method of claim 3, wherein the glucocorticoid steroid is dexamethasone.

5. The method of claim 1, wherein the glucocorticoid steroid is administered to the patient at least two days prior to administration of the imiglucerase.

6. The method of claim 1, wherein the mannose receptors on the patient's macrophage cell surfaces are selectively increased.

7. The method of claim 1, wherein the glucocorticoid steroid is administered orally, intramuscularly, intradermally, intravenously or intraperitoneally.

8. The method of claim 3, wherein the macrophage is exposed to the glucocorticoid steroid at least two days prior to exposure to the imiglucerase.

9. The method of claim 3, wherein the macrophage is in a human.

10. The method of claim 9, wherein the human has Gaucher disease.

11. The method of claim 9, wherein mannose receptors are selectively increased on the surface of the macrophage in the human.

\* \* \* \* \*

UNITED STATES PATENT AND TRADEMARK OFFICE
CERTIFICATE OF CORRECTION

PATENT NO. : 7,658,916 B2 Page 1 of 1
APPLICATION NO. : 10/408670
DATED : February 9, 2010
INVENTOR(S) : Zhu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 448 days.

Signed and Sealed this

Thirtieth Day of November, 2010

David J. Kappos
*Director of the United States Patent and Trademark Office*